(12) United States Patent
Maekawa et al.

(10) Patent No.: US 9,176,073 B2
(45) Date of Patent: Nov. 3, 2015

(54) EVALUATION SUBSTRATE, DEFECT EXAMINATION METHOD AND DEFECT DETECTION DEVICE

(71) Applicant: DAI NIPPON PRINTING CO., LTD., Tokyo (JP)

(72) Inventors: Shinji Maekawa, Tokyo (JP); Masafumi Sato, Tokyo (JP)

(73) Assignee: DAI NIPPON PRINTING CO., LTD., Tokyo (JP)

( * ) Notice: Subject to any disclaimer, the term of this patent is extended or adjusted under 35 U.S.C. 154(b) by 132 days.

(21) Appl. No.: 13/903,529

(22) Filed: May 28, 2013

(65) Prior Publication Data

US 2013/0258330 A1  Oct. 3, 2013

Related U.S. Application Data

(63) Continuation of application No. PCT/JP2011/068894, filed on Aug. 22, 2011.

(30) Foreign Application Priority Data

Nov. 29, 2010 (JP) ................. 2010-264651

(51) Int. Cl.
*H01L 21/027* (2006.01)
*G01N 21/95* (2006.01)
(Continued)

(52) U.S. Cl.
CPC ............ *G01N 21/9501* (2013.01); *G01N 21/93* (2013.01); *H01L 22/12* (2013.01); *H01L 22/30* (2013.01); *H01L 21/0276* (2013.01)

(58) Field of Classification Search
CPC ................. G01N 21/84–21/958; H01L 21/027

USPC ........................................................ 356/237.4
See application file for complete search history.

(56) References Cited

U.S. PATENT DOCUMENTS 5,523,602 A   6/1996   Horiuchi et al.
6,245,311 B1  6/2001   Kobayashi et al.
(Continued)

FOREIGN PATENT DOCUMENTS

CN   101101266 A   1/2008
EP   0989596 A1    3/2000
(Continued)

OTHER PUBLICATIONS

Office Action issued in corresponding Japanese Patent Application No. 2013-043429 dated Apr. 21, 2015.
(Continued)

*Primary Examiner* — Roy M Punnoose
(74) *Attorney, Agent, or Firm* — Pearne & Gordon LLP

(57) ABSTRACT

The present invention provides an evaluation substrate for evaluating a foreign object defect included in an organic material, a defect examination method and defect detection device. The evaluation substrate of the present invention includes a substrate, a first film arranged on the substrate, and a second film arranged on the first film, wherein a film containing an organic material is formed on the second film; the first film being set lower than an etching rate of the second film with respect to an etchant used in etching the second film, the first film having the same or a smaller detection lower limit value of an optically detectable defect than a detection lower limit value of a defect of the second film; and a thickness of the second film being set to a value near an optically measured lowest or minimum Haze value.

5 Claims, 25 Drawing Sheets

(A)

(B)

(C)

(51) Int. Cl.
*G01N 21/93* (2006.01)
*H01L 21/66* (2006.01)

(56) References Cited

U.S. PATENT DOCUMENTS

| | | | |
|---|---|---|---|
| 7,622,185 B2* | 11/2009 | Wang et al. | 428/327 |
| 7,751,005 B2* | 7/2010 | Oka et al. | 349/118 |
| 8,039,065 B2* | 10/2011 | Ikeda et al. | 428/1.32 |
| 2006/0189097 A1* | 8/2006 | Maruyama et al. | 438/458 |
| 2006/0234035 A1* | 10/2006 | Wang et al. | 428/327 |
| 2009/0115028 A1 | 5/2009 | Shimomura et al. | |
| 2012/0225265 A1* | 9/2012 | Willham | 428/201 |
| 2014/0332786 A1* | 11/2014 | Nakazawa | 257/40 |

FOREIGN PATENT DOCUMENTS

| | | |
|---|---|---|
| JP | S61-161796 A | 7/1986 |
| JP | H06-268184 A | 9/1994 |
| JP | H07-122719 A | 5/1995 |
| JP | H09-115973 A | 5/1997 |
| JP | H09-134940 A | 5/1997 |
| JP | H10-242015 A | 9/1998 |
| JP | H11-354529 A | 12/1999 |
| JP | 2000-040828 A | 2/2000 |
| JP | 2001-305073 A | 10/2001 |
| JP | 2003-179107 A | 6/2003 |
| JP | 2005-241963 A | 9/2005 |
| JP | 2005-257576 A | 9/2005 |
| JP | 2006-112871 A | 4/2006 |
| JP | 2008-113027 A | 5/2008 |
| JP | 2008-164336 A | 7/2008 |
| JP | 2009-135437 A | 6/2009 |
| JP | 2010-191416 A | 9/2010 |
| WO | 9857361 A1 | 12/1998 |

OTHER PUBLICATIONS

International Search Report for PCT/JP2011/068894 dated Nov. 1, 2011.
Non-Final Office action for JP Application No. 2012-507506 dated Jun. 5, 2012.
Non-Final Office action for JP Application No. 2012-507506 dated Nov. 13, 2012.
Office Action issued in corresponding Chinese Patent Application No. 2011800571110 dated Sep. 28, 2014.
Written Opinion issued in Application No. PCT/JP2011/068894 dated Nov. 1, 2011.

* cited by examiner

FIG.7A

| Film thickness (nm) | Haze value (ppm) |
|---|---|
| 140 | 5.5 |
| 145 | 9.4 |
| 150 | 23.9 |
| 155 | 60 |
| 160 | 160 |

FIG.7C

| Haze value (ppm) | Lower detection limit (μ m) |
|---|---|
| 6 | 1.2 |
| 30 | 1.4 |
| 40 | 1.4 |
| 50 | 1.6 |
| 60 | 1.7 |

FIG.8A

Lot A  Film formation temperature : 615°C

| Boat number | Film thickness (nm) | Haze value (ppm) |
|---|---|---|
| 61 | 149.5 | 19.68 |
| 57 | 150.2 | 24.71 |
| 53 | 150.6 | 24.53 |
| 49 | 150.4 | 23.63 |
| 45 | 149.9 | 21.58 |
| 41 | 149.5 | 18.58 |
| 37 | 149.2 | 16.15 |
| 33 | 149.0 | 14.97 |
| 29 | 149.1 | 15.44 |
| 25 | 149.7 | 17.62 |
| 21 | 151.6 | 26.05 |
| 17 | 154.5 | 55.86 |
| 13 | 157.1 | 76.42 |

Heating temperature
U  :616.5
CU :615.0
CL :612.0
L  :603.2

FIG.8B

Lot B   Film formation temperature : 620°C

| Boat number | Film thickness (nm) | Haze value (ppm) |
|---|---|---|
| 29 | 150.7 | 24.44 |
| 25 | 151.6 | 29.2 |
| 21 | 153.5 | 44.94 |
| 17 | 156.5 | 85.1 |
| 13 | 159.2 | 142.46 |

Heating temperature
U   :621.5
CU  :620.0
CL  :617.0
L   :604.2

FIG.8C

Lot C   Film formation temperature : 620°C

| Boat number | Film thickness (nm) | Haze value (ppm) |
|---|---|---|
| 61 | 147.1 | 13.81 |
| 57 | 148.5 | 18.44 |
| 53 | 149.4 | 22.07 |
| 49 | 149.7 | 23.66 |
| 45 | 149.7 | 22.80 |
| 41 | 149.8 | 23.57 |
| 37 | 150.0 | 23.98 |
| 33 | 150.3 | 24.21 |
| 29 | 150.8 | 26.36 |
| 25 | 151.9 | 32.05 |
| 21 | 154.2 | 50.50 |
| 17 | 157.7 | 95.88 |
| 13 | 161.0 | 150.46 |

Heating temperature
U   :621.5
CU  :620.0
CL  :617.0
L   :604.2

FIG.8D

Lot D  Film formation temperature : 620°C

| Boat number | Film thickness (nm) | Haze value (ppm) |
|---|---|---|
| 61 | 145.1 | 9.44 |
| 57 | 146.4 | 12.00 |
| 53 | 147.3 | 14.81 |
| 49 | 147.9 | 16.88 |
| 45 | 148.3 | 17.77 |
| 41 | 148.9 | 24.91 |
| 37 | 149.8 | 20.48 |
| 33 | 150.7 | 30.63 |
| 29 | 152.0 | 40.40 |
| 25 | 153.6 | 57.04 |
| 21 | 156.4 | 100.03 |
| 17 | 160.3 | 200.65 |
| 13 | 163.6 | 311.79 |

Heating temperature
U   : 621.5
CU  : 620.0
CL  : 617.0
L   : 608.0

FIG.8E

Lot E   Film formation temperature : 620°C

| Boat number | Film thickness (nm) | Haze value (ppm) |
|---|---|---|
| 61 | 139.9 | 5.2 |
| 57 | 140.3 | 6.5 |
| 53 | 135.5 | 7.4 |
| 49 | 129.6 | 13.5 |

Heating temperature
U   :621.5
CU  :620.0
CL  :617.0
L   :604.2

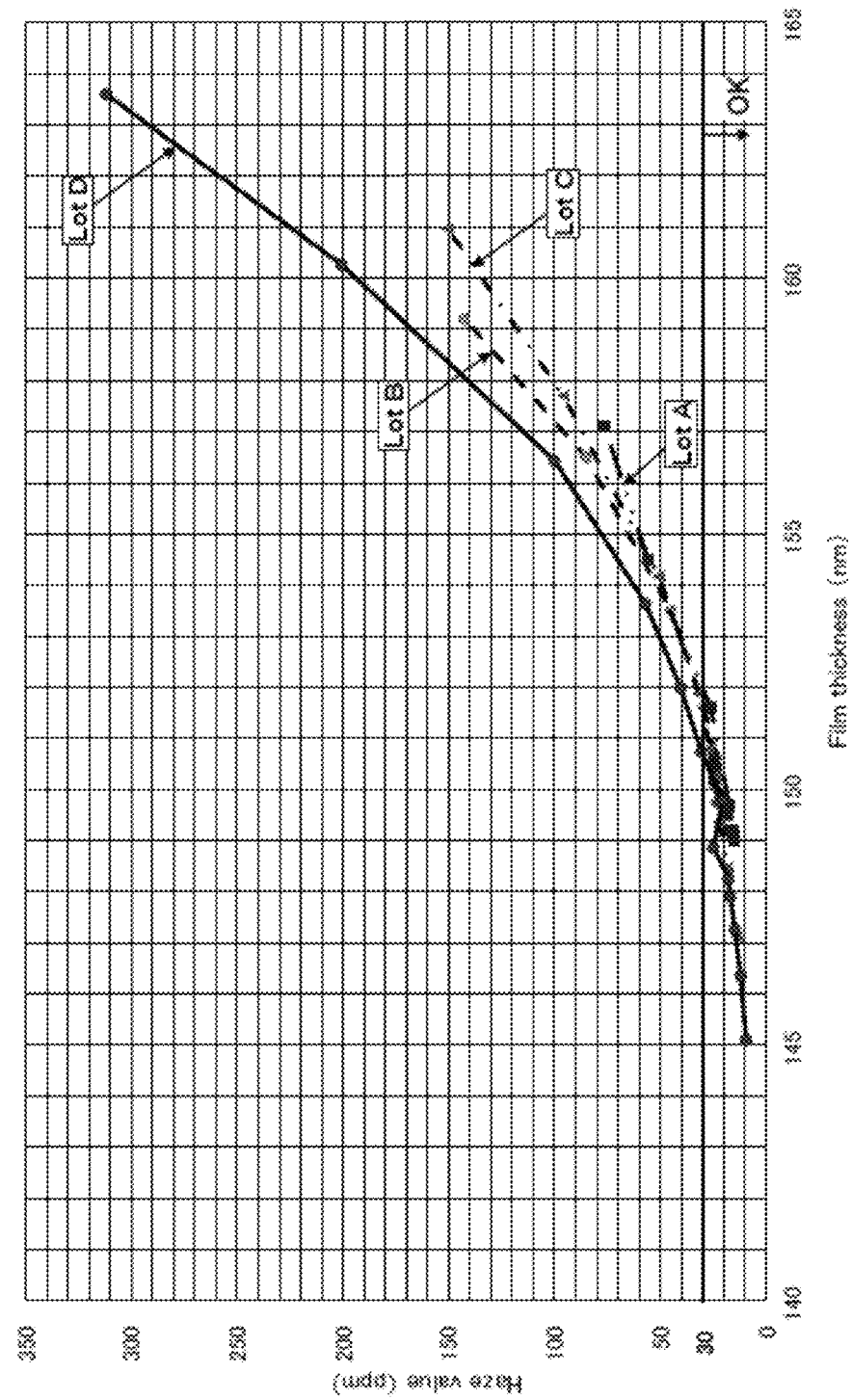

FIG.11A

Lot F  Film formation temperature : 615°C

| Film thickness (nm) | Haze value (ppm) |
|---|---|
| 139.9 | 5.52 |
| 139.7 | 5.477 |
| 139.5 | 5.453 |
| 139.2 | 5.484 |
| 140.3 | 5.647 |
| 140.0 | 5.576 |
| 139.8 | 5.545 |
| 139.5 | 5.549 |
| 139.5 | 5.511 |
| 135.5 | 6.292 |
| 135.3 | 6.438 |
| 135.1 | 6.538 |
| 134.9 | 6.947 |
| 134.8 | 6.931 |
| 129.8 | 14.058 |
| 129.6 | 14.701 |
| 129.3 | 15.37 |
| 129.1 | 16.044 |
| 129.1 | 15.849 |

FIG.12

Lot G  Film formation temperature : 610°C

| Film thickness (nm) | Haze value (ppm) |
|---|---|
| 148.1 | 8.5 |
| 148.5 | 9.8 |
| 149.1 | 11.9 |
| 149.5 | 12.7 |
| 150.2 | 15.6 |
| 150.5 | 16.3 |
| 151.2 | 19.8 |

(A)

| Haze value (ppm) | Ra (nm) |
|---|---|
| 10 | 1.726 |
| 30 | 1.701 |
| 110 | 2.256 |
| 160 | 2.47 |

| Film types of single layer formed on a silicon substrate | Lower limit of the detection sensitivity of an optical defect examination device |
|---|---|
| Th-SiO$_2$ | No less than 60nm |
| Si$_3$N$_4$ | No less than 80nm |
| Polysilicon | No less than 130nm |
| TEOS | No less than 75nm |
| Resist Film | No less than 75nm |
| Ta | No less than 80nm |
| Cu PVD | No less than 80nm |
| TiN/Ti | No less than 80nm |
| SOI | No less than 50nm |
| Amorphous Silicon | No less than 100nm |

EVALUATION SUBSTRATE, DEFECT EXAMINATION METHOD AND DEFECT DETECTION DEVICE

CROSS-REFERENCE TO RELATED APPLICATIONS

This application is a U.S. continuation application filed under 35 USC 111(a) claiming benefit under 35 USC 120 and 365(c) of PCT application PCT/JP2011/068894, filed on Aug. 22, 2011, and the benefit of priority from the prior Japanese Patent Application No. 2010-264651, filed on Nov. 29, 2010, the entire contents of which are incorporated herein by reference.

FIELD

The present invention is related to an evaluation substrate for evaluating a foreign object defect included in an organic material, a defect examination method and a defect detection device.

BACKGROUND

When manufacturing a semiconductor device, miniature processing is performed by lithography using a photo resist. In recent years, the high integration of semiconductor devices is proceeding and there is a tendency for the activated light rays which are used to have short wave lengths to a KrF excimer laser (248 nm), ArF excimer laser (193 nm) and F2 excimer laser (157 nm). In a lithography process using these light sources, a problem is produced whereby the dimension accuracy of a photo resist pattern drops due to the effects of a standing wave due to the reflection of exposure light of the substrate or the effects of scattered reflection of the exposure light due to unevenness of the substrate. Thus, a method for arranging a Bottom Anti-Reflective Coating (BARC) film between the photo resist and the substrate to be processed as been examined.

For example, an inorganic bottom anti-reflective coating such as titanium, titanium dioxide, titanium nitride, chrome oxide, carbon, or $\alpha$-silicon, and an organic bottom anti-reflective coating comprised from a light adsorption material and a high molecular compound are known as bottom anti-reflective coatings. While an inorganic bottom anti-reflective coating requires equipment such as a vacuum deposition device, CVD device and sputtering device for forming a film, an organic bottom anti-reflective coating does not require any special equipment and is therefore advantageous. As a result, numerous examinations have taken place into organic bottom anti-reflective coatings. For example, an acryl resin type bottom anti-reflective coating which includes a hydroxyl group which is a cross-linking reaction group, and a light adsorption group within the same molecule or a novolac resin type bottom anti-reflective coating which includes a hydroxyl group which is a cross-linking reaction group, and a light adsorption group within the same molecule can be exemplified.

These organic bottom anti-reflective coatings are often formed using a thermosetting composition since the coating prevents intermixing with a photo resist coated upon it. As a result, the bottom anti-reflective coating becomes insoluble in a photo resist developer solution and it is necessary to remove the bottom anti-reflective using dry etching coating prior to processing a semiconductor substrate.

Furthermore, a bottom anti-reflective coating formation composition which has excellent dry etching tolerance, high anti-reflective effects and does not produce intermixing with a resist is described as an organic bottom anti-reflective coating for example in Japanese Laid Open Patent 2005-241963.

The amount and size of foreign objects included in the material of an organic bottom anti-reflective coating used in the manufacture of a semiconductor device affects the manufacture of the semiconductor device. Thus, it is desirable to ascertain data relating to quantifying the foreign objects included in the material of an organic bottom anti-reflective coating formed in an actual semiconductor device. Quality during manufacture of a semiconductor device is assured by establishing technology for evaluating the quality of a bottom anti-reflective coating when applied to a semiconductor device. However, the current situation is that a technology for evaluating the quality of a bottom anti-reflective coating has not been established.

The present invention attempts to solve the problems described above by providing an evaluation substrate for evaluating defects caused by foreign objects included within an organic material which affects the manufacture of a semiconductor device, a defect examination method and a defect detection device.

SUMMARY

The inventors of the present invention arrived at the present invention as a result of keen examination by developing a technology for optically detecting foreign materials included in an organic material. The present invention encompasses the following forms. An evaluation substrate related to one embodiment of the present invention includes a substrate, a first film arranged on the substrate, and a second film arranged on the first film, wherein a film containing an organic material is formed on the second film; an etching rate of the first film being set lower than an etching rate of the second film with respect to an etchant used in etching the second film, the first film having the same or a smaller detection lower limit value of an optically detectable defect than a detection lower limit value of a defect of the second film; and a thickness of the second film being set so as to have a value near an optically measured lowest or minimum Haze value. According to the evaluation substrate, it is possible to quantitatively evaluate foreign material included in an organic material formed on an actual semiconductor device, for example, an organic bottom anti-reflective coating coated on a substrate to be processed.

An evaluation substrate related to one embodiment of the present invention includes a silicon substrate, a silicon oxide film arranged on the silicon substrate, and a polysilicon film arranged on the silicon oxide film, a Haze value of a surface of the polysilicon film being 30 ppm or less. Accordingly, it is possible to provide an evaluation substrate for evaluating defects caused by foreign materials included in an organic material.

An evaluation substrate related to one embodiment of the present invention includes a silicon substrate, a silicon oxide film arranged on the silicon substrate, and a polysilicon film arranged on the silicon oxide film and a thickness of the polysilicon film being set so as to have a value near an optically measured lowest or minimum Haze value. Accordingly, it is possible to provide an evaluation substrate for evaluating defects caused by foreign materials included in an organic material.

An evaluation substrate related to one embodiment of the present invention includes a substrate, a silicon oxide film arranged on the silicon substrate, and an amorphous silicon film arranged on the silicon oxide film and a thickness of the amorphous silicon film being set so as to have a value near an optically measured lowest or minimum Haze value. Accordingly, it is possible to provide an evaluation substrate for evaluating defects caused by foreign materials included in an organic material.

In addition, in the evaluation substrate related to one embodiment of the present invention, an average surface roughness (Ra) of the polysilicon film or the amorphous silicon film may be 1.73 nm or less. According to the evaluation substrate, it is possible to reduce a detection lower limit value of a foreign material defect.

In addition, in the evaluation substrate related to one embodiment of the present invention, a largest high and low difference (P–V value) of the polysilicon film or the amorphous silicon film may be 13.8 nm or less. According to the evaluation substrate, it is possible to reduce a detection lower limit value of a foreign material defect.

In addition, in the evaluation substrate related to one embodiment of the present invention, a square surface roughness (RMS) of the polysilicon film or the amorphous silicon film may be 2.2 nm or less. According to the evaluation substrate, it is possible to reduce a detection lower limit value of a foreign material defect.

In addition, in the evaluation substrate related to one embodiment of the present invention, a thickness of the polysilicon film or the amorphous silicon film may be larger than a thickness of the silicon oxide film. According to the evaluation substrate, it is possible to reduce a detection lower limit value of a foreign material defect.

A defect examination method related to one embodiment of the present invention is a method of detecting a defect by detecting using a foreign object included in an organic material, the method including preparing a silicon substrate, optically detecting a defect on a surface of the silicon substrate and storing data of a position for each detected defect as first defect data, optically detecting a defect on a surface of a silicon oxide film formed on the silicon substrate and storing data of a position for each detected defect as second defect data, calculating first difference defect data by deleting a defect at the same position as the position for the first defect data from the second defect data, optically detecting a defect on a surface of a polysilicon film formed on the silicon oxide film and storing data of a position for each detected defect as third defect data, calculating second difference defect data by deleting a defect at the same position as the position for the first difference defect data from the third defect data, etching a film including an organic material formed on the polysilicon film, the organic material being derived from a raw material having an organic material as a main component, etching the polysilicon film, detecting a defect being a cause of an etching residue on the silicon oxide film, and storing defect data of a position for each detected defect as fourth defect, and obtaining a number of defects in a film including the organic material by deleting a defect at the same position as the position for the second difference defect data from the fourth defect data. According to the defect examination method it is possible to extract and evaluate defects caused by foreign materials included in an organic material in a manufacturing process of a semiconductor device.

A defect examination method related to one embodiment of the present invention is a method of detecting a defect by detecting using a foreign object included in an organic material, the method including optically detecting a defect on a surface of a first film formed on a substrate and storing data of a position for each detected defect as first defect data, optically detecting a defect on a surface of a second film formed on the first film and storing data of a position for each detected defect as second defect data, calculating difference defect data by deleting a defect at the same position as the position for the first defect data from the second defect data, etching a film including an organic material formed on the second film, the organic material being derived from a raw material having an organic material as a main component, and etching the second film using an etchant having a higher etching rate with respect to the second film than to the first film, detecting a defect being a cause of an etching residue on the first film, and storing data of a position for each detected defect as third defect, and obtaining a number of defects in a film including the organic material by deleting a defect at the same position as the position for the difference defect data from the third defect data. According to the defect examination method it is possible to extract and evaluate defects caused by foreign materials included in an organic material in a manufacturing process of a semiconductor device.

A defect detection device related to one embodiment of the present invention includes a defect detection means including a light source, a stage fixed with an object to be irradiated with light emitted from the light source, and a light detection part configured to detect reflection light of the light emitted from the object, and a defect data process means configured to process defect data for each position of a surface of the object obtained from the defect detection part, the defect data process means further including a first storage part configured to store defect data for each position of the surface of the object detected by the defect detection means, a comparison operation means configured to compare defect data for each position of a surface of a first object with defect data for each position of a surface of a second object, the second object being the first object undergoing a predetermined process, to perform a difference operation for each defect at the same position, and to extract a defect being a cause of the predetermined process upon the second object, and a second storage part configured to store defect data calculated and extracted by the comparison operator. According to the defect detection device, it is possible to quantitatively evaluate foreign material included in an organic material formed on an actual semiconductor device, for example, an organic bottom anti-reflective coating coated on a substrate to be processed.

According to the present invention, it is possible to extract and evaluate defects caused by foreign objects included in an organic material.

BRIEF DESCRIPTION OF THE DRAWINGS

FIG. 7A is a diagram showing the relationship between the film thickness of a polysilicon film of the evaluation substrate and a Haze value related to one embodiment of the present invention;

FIG. 7C is a diagram showing the relationship between the Haze value and a defect detection lower limit value related to one embodiment of the present invention;

FIG. 8A is a table showing the results of measuring a film formation temperature of a polysilicon film for each slot of the LPCVD device in FIG. 4 and a Haze value;

FIG. 8B is a table showing the results of measuring a film formation temperature of a polysilicon film for each slot of the LPCVD device in FIG. 4 and a Haze value;

FIG. 8C is a table showing the results of measuring a film formation temperature of a polysilicon film for each slot of the LPCVD device in FIG. 4 and a Haze value;

FIG. 8D is a table showing the results of measuring a film formation temperature of a polysilicon film for each slot of the LPCVD device in FIG. 4 and a Haze value;

FIG. 8E is a table showing the results of measuring a film formation temperature of a polysilicon film for each slot of the LPCVD device in FIG. 4 and a Haze value;

FIG. 9 is a graph plotting the measurement results of FIGS. 8A~8D;

FIG. 11A is a table showing the measurement results of a film thickness of and Haze value for a polysilicon film;

FIG. 12 is a table showing the results of measuring film thickness of a polysilicon film and a Haze value when a film formation temperature is reduced;

FIG. 18 is a table showing general detection sensitivity of an optical defect examination device with regards to the major film types of single layer formed on a silicon substrate.

DESCRIPTION OF EMBODIMENTS

Figure 1:
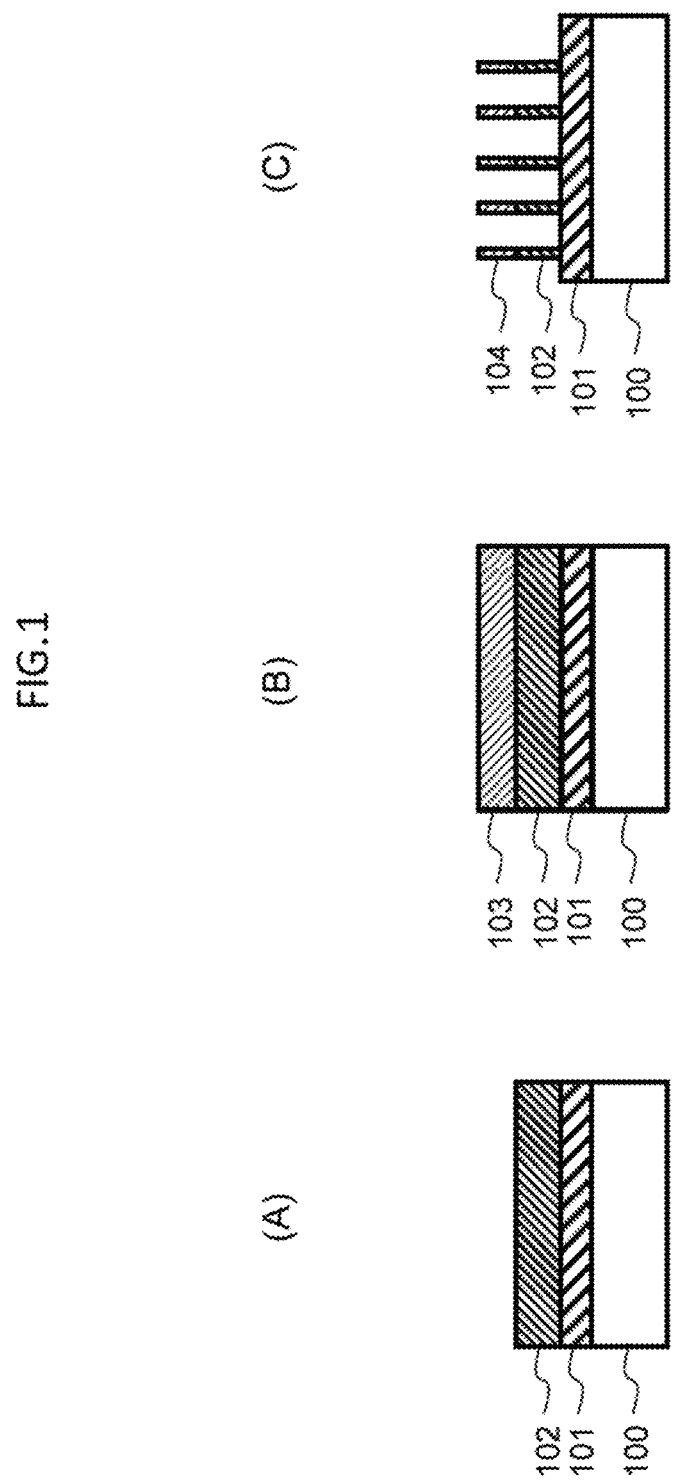
FIG. 1 is a schematic view diagram showing an example of the structure of an evaluation substrate and an examination process using the evaluation substrate related to one embodiment of the present invention.

Before explaining the embodiments for realizing the present invention, the circumstances leading to the present invention will be briefly explained while illustrating the relationship with conventional technology in order to better clarify the characteristics of the present invention.
(Circumstances Leading to the Invention)

An organic bottom anti-reflective coating is coated between a photo resist and a substrate to be processed. However, defects are sometimes produced in the surface of the organic bottom anti-reflective coating. These defects affect the manufacturing process of a semiconductor device due to foreign objects included in the organic bottom anti-reflective coating.

Conventionally, in order to quantitatively evaluate foreign objects included in an organic material used in the manufacture of a semiconductor device, there was no option other than to chemically analyze the organic material itself before being used in the manufacture process. That is, quantitative evaluation of foreign objects included in an organic material was performed as one way of material evaluation using a chemical means. However, when manufacturing a semiconductor device while it was necessary to evaluate the properties of an organic material film formed on an actual semiconductor device, the inventors of the present invention were not aware of a means for meeting this necessity. Thus, the inventors of the present invention examined ascertaining quantifying the cause of defects included in an organic material by a physical means using optical analysis. In addition, the inventors of the present invention were able to ascertain defects during formation of an organic bottom anti-reflective coating and by a comparison examination of the defects were able to find out defects arising in the material of an organic bottom anti-reflective coating.

However, because polysilicon which is used as a gate electrode in a semiconductor device has a larger detection lower limit value of a defect when adhering a film to a substrate compared to other materials, it was particularly difficult to identify objects which should be judged as defects during the manufacture process of a semiconductor device. Thus, as a result of keen examination, the inventors of the present invention were successful in lowering the detection lower limit of a defect in polysilicon used in a gate electrode etc. At this time, it was clear that there is a correlation between a [Haze value] of a surface detected by a defect examination device and a detection lower limit. Furthermore, a Haze value is a Haze Average value and in the measurement of a Haze value described below, an Average value is called a Haze value.

A [Haze value] is calculated using the formula (1) below.

$$\text{Haze} = k(\text{PMT amount of light received/amount of specular reflected light}) \times 10^6 \text{ ppm} \quad (1)$$

However, k: is a constant inherent to a defect examination device including received light efficiency etc.

Amount of specular reflected light: is a logical value in the case where laser light does not scatter in a silicon substrate surface.

PMT amount of light received: is the amount of scattered light received by a PMT (Photo-Multiplier Tube).

Furthermore, measurement of a Haze value described in the present specification is performed using a SP1 DLS manufactured by KLA-Tencor.

An evaluation substrate and manufacturing method of the evaluation substrate related to the present invention are explained below while referring to the diagrams. However, the evaluation substrate of the present invention can be realized by many modified forms and should not be interpreted as being restricted by the contents described in the embodiments illustrated below.

<Manufacturing Process and Examination Process of an Evaluation Substrate>

Figure 2:
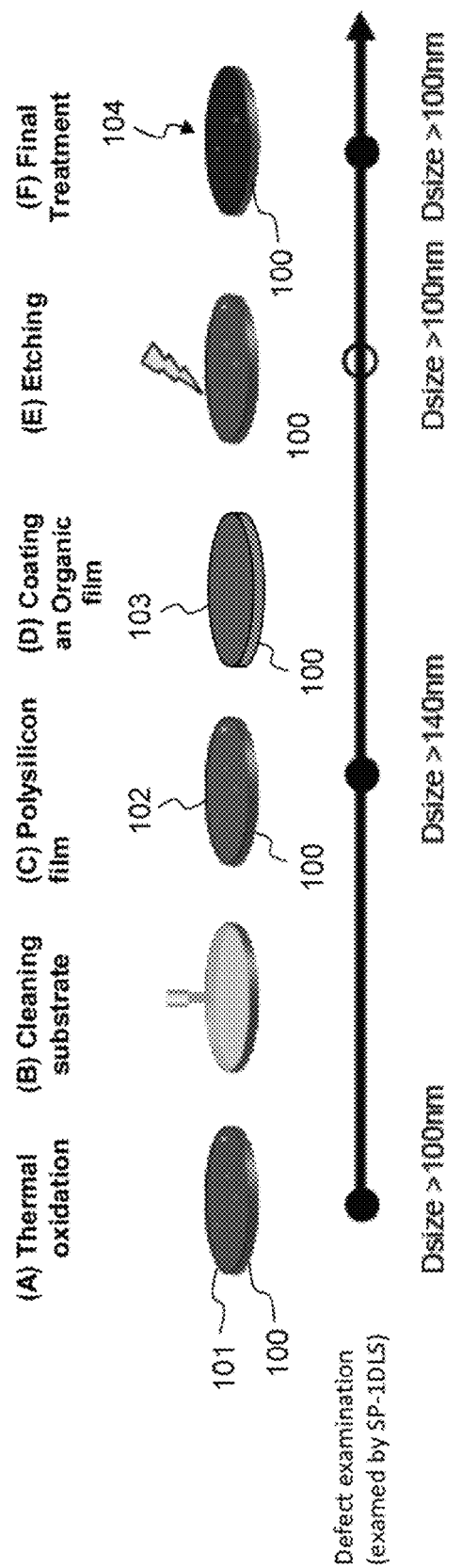
FIG. 2 is a diagram showing a manufacturing process of the evaluation process shown in FIG. 1.

First, a structural example, a manufacturing process and examination process of an evaluation substrate is explained while referring to FIG. 1 and FIG. 2. FIG. 1 is a cross-sectional diagram which exemplarily shows an example of a structure of an evaluation substrate and an examination process using the evaluation substrate. FIG. 2 is a diagram which shows an example of a manufacturing process and examination process of FIG. 1. Furthermore, the evaluation substrate shown in FIG. 1 is a substrate modeled on a semiconductor device and example whereby polysilicon is used as a gate electrode is shown.

In FIG. 1 (A), an oxide film ($SiO_2$) 101 and a polysilicon film 102 are stacked in this order on a silicon substrate 100. The oxide film 101 is a film modeled on a gate insulation film and is an etching stopper in the present examination process. The polysilicon film can be used as a gate electrode. Then, in FIG. 1 (B), an organic bottom anti-reflective coating 103 is formed on the polysilicon film 102 by a spin coat method for example. Then, in FIG. 1 (C), the polysilicon film 102 and the organic bottom anti-reflective coating 103 are etched by dry etching. In the case where foreign materials exist on the organic bottom anti-reflective coating, the parts where the foreign materials exists function as a mask and residue 104 is obtained. Furthermore, the present invention is not limited to the oxide film ($SiO_2$) 101, for example, a nitride film ($SiN_x$) or a plurality of stacked insulation films may also be used.

Then, the manufacturing process and examination process of the evaluation substrate shown in FIG. 1 is explained while referring to FIG. 2.

(1) Defect Examination of a Silicon Substrate

First, a silicon substrate 100 (bare silicon substrate) is prepared and defects on the surface are examined. In this examination, the surface of the silicon substrate is scanned with a laser using a defect examination device (For example, a SP1 DLS manufactured by KLA-Tencor), defects larger than a predetermined size (100 nm for example) are detected and the number of detected defects and data related to the coordinates of each defect are stored as first defect data. The silicon substrate 100 is cleaned after the defect examination.

(2) Formation of an Oxide Film (Refer to FIG. 2 (A))

The silicon substrate 100 after cleaning is inserted into a thermal oxidation furnace and an oxide film ($SiO_2$) 101 is formed on the surface of the silicon substrate 100 under predetermined conditions (heating temperature and oxide gas flow amount settings etc). The detection sensitivity of the defect examination device changes according to a combination of optical characteristics of two types of film and a film thickness may be selected so that detection sensitivity increases. In the present process, the optical characteristics when a laser light source wavelength is 488 nm are n=4.476 and k=0.248 and in the case where the thickness of the polysilicon film is 150 nm for example, the thickness of the oxide film 101 is appropriately set within a range of 60 nm~130 nm or more preferably 80 nm~100 nm.

Figure 3:
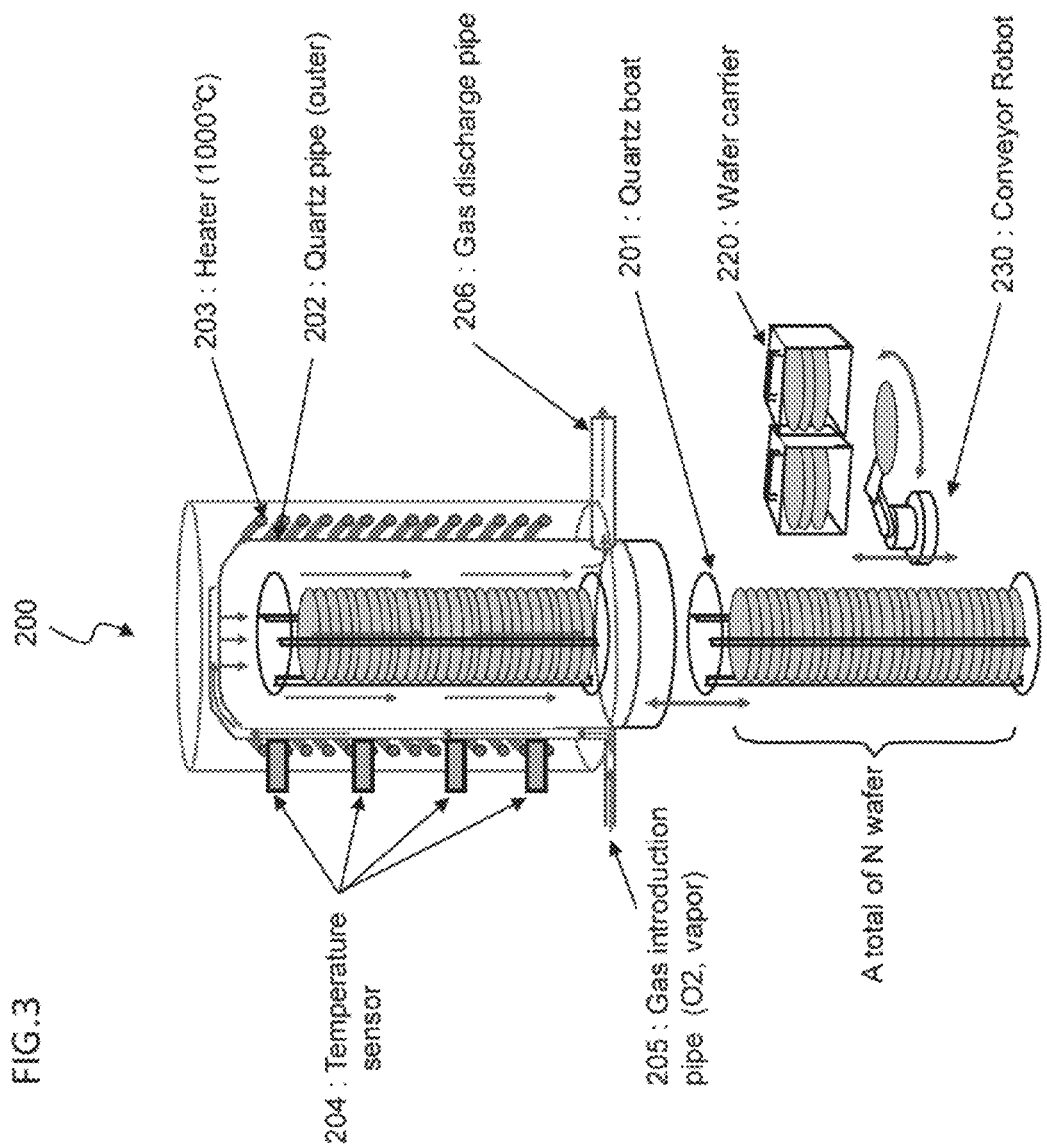
FIG. 3 is a diagram showing the structure of thermal oxidation furnace which forms an oxide film.

The film formation process of the oxide film using the thermal oxidation furnace is explained while referring to FIG. 3. In FIG. 3, the thermal oxidation furnace 200 is arranged with a quartz boat 201, a quartz pipe (outer) 202, a heater 203, a temperature sensor 204, a gas introduction pipe 205 and a gas discharge pipe 206.

The silicon substrate is transferred from a wafer carrier 220 by a conveyor robot 230 and set on the quartz boat 201. The quartz boat 201 is arranged for example with a boat on which prescribed number of silicon substrates for processing are set. After the silicon substrate is set, the quartz boat 201 is inserted into the quartz pipe 202. Following this, the quartz pipe 202 is sealed and the air inside of the quartz pipe 202 is removed using a vacuum pump (not shown in the diagram) until the vacuum level inside of the quartz pipe 202 reaches to a predetermined vacuum level. Then, the temperature inside of the quartz pipe 202 is raised to about 1000° C. by the heater 203, $O_2$ and $H_2O$ are introduced from the gas introduction pipe 205 and an oxide film is formed. The temperature inside the quartz pipe 202 is detected using the temperature sensor 204 arranged at four positions as shown in the diagram. The drive state of the heater 203 is controlled according to the temperature detected by these temperature sensors 204 and the temperature within the quartz pipe 202 is adjusted to a set temperature. Then, the temperature inside of the quartz pipe 202 is turned down and returned to an atmospheric state, the seal is released and the quartz boat 201 is lifted from the quartz pipe 202. Then, the silicon substrate set on the quartz boat 201 is transferred to the wafer carrier 220 by the conveyor robot 230.

(3) Defect Examination of an Oxide film (refer to FIG. 2 (A))

Then, defects on the surface of the oxide film 101 are examined. In this examination, the surface of the oxide film 101 is scanned with a laser using a defect examination device (For example, a SP1 DLS manufactured by KLA-Tencor), defects larger than 100 nm are detected and the number of detected defects and data related to the coordinates of each defect are stored as second defect data.

(4) Substrate Cleaning (refer to FIG. 2 (B))

Following completion of the examination in (3) described above, the silicon substrate 100 attached with the oxide film 101 is cleaned.

(5) Formation of a Polysilicon Film (refer to FIG. 2 (C))

The silicon substrate 100 attached with the oxide film 101 after cleaning is prepared using a CVD method (Chemical Vapor Deposition). It is preferable to adopt a LPCVD method (Low Pressure Chemical Vapor Deposition) in which a film formation temperature is set to a comparatively low temperature (650° C. or less) so that the film formation can be controlled at a low formation rate. The silicon substrate 100 attached with the oxide film 101 is inserted into a LPCVD device and the polysilicon film 102 is formed on the oxide film 101 under predetermined conditions (film formation temperature and film thickness settings etc). As described above, the detection sensitivity of the defect examination device changes according to a combination of optical characteristics of two types of film and a film thickness may be selected so that detection sensitivity increases. In the present process, the optical characteristics when a laser light source wavelength is 488 nm are n=4.476 and k=0.248 and in the case where the thickness of the oxide film 101 is 80 nm for example, the thickness of the polysilicon film 102 is appropriately set within a range of 128 nm~153 nm or more preferably 140 nm~145 nm.

The polysilicon film 102 which is formed is preferred to have a surface Haze value of 30 ppm or less. By having a Haze value of 30 ppm it is possible to set the defect lower limit value to 140 nm or less and it is possible to improve the S/N ratio of defect detection of foreign materials included in an organic bottom anti-reflective coating. There is a correlation relationship between the film thickness of the polysilicon film 102 and a Haze value and in the case where the Haze value varies depending on the defect examination device which is used, it is preferred that the film thickness of the polysilicon film 102 is set so that the Haze value which is measured using the defect examination device becomes near to a lowest or minimum. Furthermore, "near" refers to a film thickness range in which the Haze value allows the detection lower limit to reach a desired value.

Figure 4:
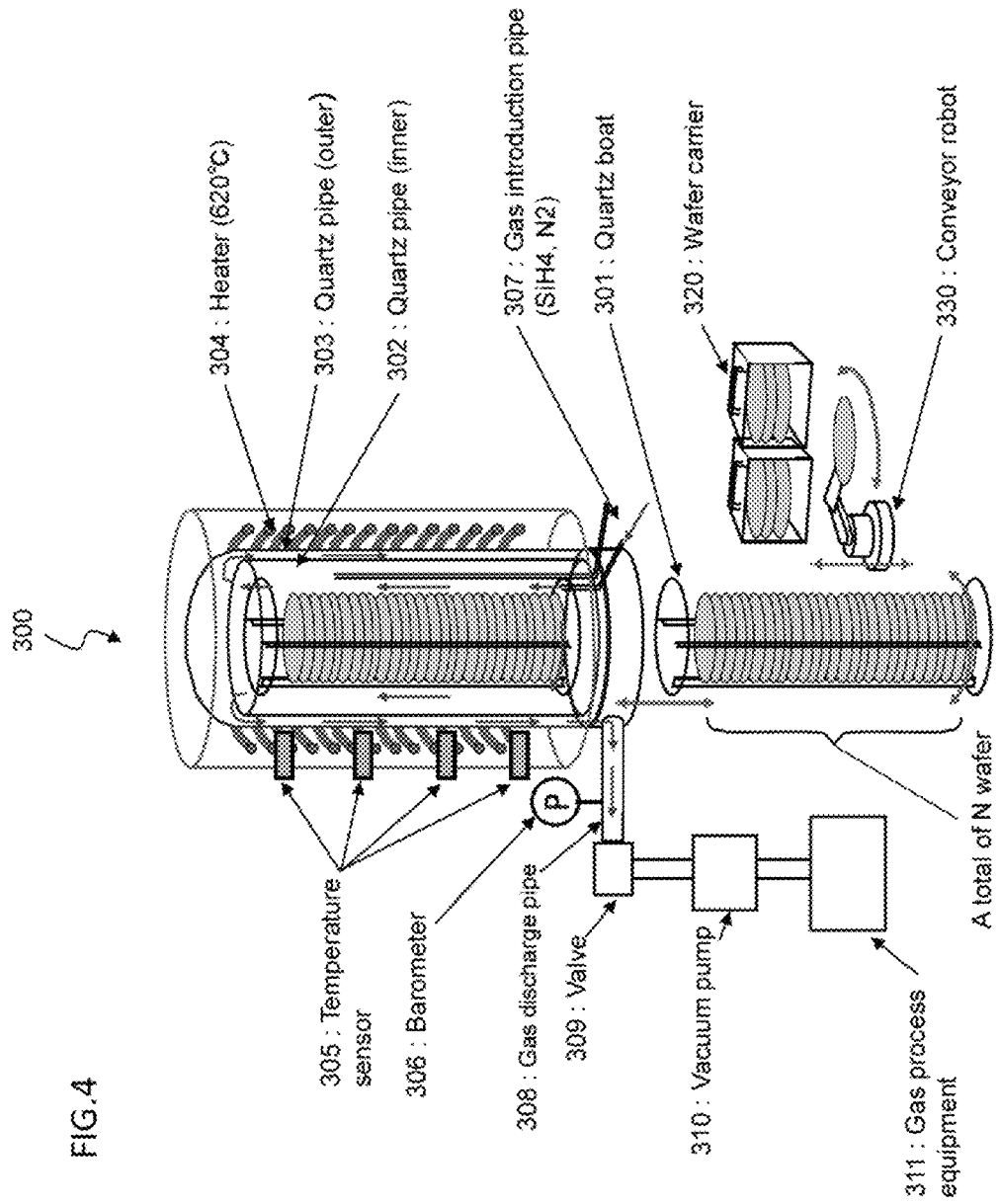
FIG. 4 is a diagram showing the structure of a LPCVS device which forms a polysilicon film.

Then, a film formation example of a polysilicon film using a LPCVD device is explained while referring to FIG. 4. In FIG. 4, the LPCVD device 300 is arranged with a quartz boat 301, a quartz pipe (inner) 302, a quartz pipe (outer) 303, a heater 304, a temperature sensor 305, a barometer 306, a gas introduction pipe 307, a gas discharge pipe 308, a valve 309, a vacuum pump 310 and gas process equipment 311.

The silicon substrate is transferred from a wafer carrier 320 by a conveyor robot 330 and set on the quartz boat 301. The quartz boat 301 is arranged for example with a boat on which the predetermined number of pieces of silicon substrates for processing are set. After the silicon substrates are set, the quartz boat 301 is inserted into the quartz pipe (inner) 302. Following this, the quartz pipe 303 (outer) is sealed and air is removed from the quartz pipe 302 (inner) until the vacuum level in the quartz pipe 302 reaches a predetermined level using the vacuum pump 310. The vacuum level within the quartz pipe 302 (inner) is measured by the barometer 306. The drive state of the vacuum pump 310 is controlled by the measured vacuum level and the vacuum level within the quartz pipe 302 (inner) is adjusted to a set value. Then, the temperature inside of the quartz pipe 302 (inner) is raised to about 620° C. by the heater 304, $SiH_4$ (silane) gas is introduced from the gas introduction pipe 307 and a polysilicon film is formed. The temperature inside the quartz pipe 302 is detected using the temperature sensor 305 arranged at four positions as shown in the diagram. The drive state of the heater 304 is controlled according to the temperature detected by these temperature sensors 305 and the temperature within the quartz pipe 302 is adjusted to a set temperature. Then, the temperature inside of the quartz pipe 302 is turned down, $N_2$ gas is introduced from the gas introduction pipe 307 and the quartz pipe 302 is returned to an atmospheric state. Then, the sealed quartz pipe 303 (outer) is released and the quartz boat 301 is lifted down from the quartz pipe 302. Then, the silicon substrate set on the quartz boat 301 is transferred to the wafer carrier 320 by the conveyor robot 330.

(6) Defect Examination of the Polysilicon Film (refer to FIG. 2 (C))

Then, defects on the surface of the polysilicon film 102 are examined. In this examination, the surface of the polysilicon film 102 is scanned with a laser using a defect examination device (For example, a SP1 DLS manufactured by KLA-Tencor), defects larger than an allowable defect size (for example 140 nm) in manufacture of a semiconductor device are detected and the number of detected defects and data related to the coordinates of each defect are stored as third defect data. Usually, the defect detection lower limit becomes less than a desired value when the silicon substrate 100 is a bare silicon and when the oxide film 101 is formed on the silicon substrate 100. The effects of the defect detection lower limit of the polysilicon film 102 become dominant at the point where the polysilicon film 102 is stacked on the oxide film 101 and in the case where the defect detection lower limit is high, the defect detection accuracy of the following organic bottom anti-reflective coating becomes worse. In the present invention, it is possible to decrease a Haze value of a surface of a polysilicon film and a defect detection lower limit and to secure defect detection accuracy of a following organic bottom anti-reflective coating.

(7) Coating of an Organic Bottom Anti-reflective Coating (refer to FIG. 1 (B) and FIG. 2 (D)).

Then, a material for forming an organic bottom anti-reflective coating is coated on the polysilicon film 102 using a spin coat method for example and the organic bottom anti-reflective coating 103 is formed. The thickness of the organic bottom anti-reflective coating 103 is about 100 nm for example.

(8) Etching (refer to FIG. 1 (C) and FIG. 2 (E))

Then, the polysilicon film 102 and the organic bottom anti-reflective coating 103 are etched using wet etching or dry etching. Preferably, the polysilicon film 102 and the organic bottom anti-reflective coating 103 are etched using dry etching. The parts which include foreign material on the organic bottom anti-reflective coating 103 become residue 104.

(9) Defect Examination after Etching

Then, defects on the surface of the silicon substrate 100 after etching are examined. In this examination, the surface of the silicon substrate 100 is scanned with a laser using a defect examination device (For example, a SP1 DLS manufactured by KLA-Tencor), defects due to the etching residue larger than for example 100 nm are detected and the number of detected defects and data related to the coordinates of each defect are stored as fourth defect data.

(10) Detection Process of Defects in the Bottom Anti-reflective Coating

Then, the coordinates of each defect detected from the surface of the oxide film 101 and stored, the coordinates of each defect detected from the surface of the polysilicon film 102 and stored are compared with the coordinates of each defect detected and stored after etching. Using this comparison, defects of which coordinates correspond to the defect coordinates of the oxide film surface and the defect coordinates of the polysilicon film surface are deleted among the defects detected after etching, and any finally remaining defects are detected as defects caused by foreign materials included bottom anti-reflective film 103.

Figure 5:
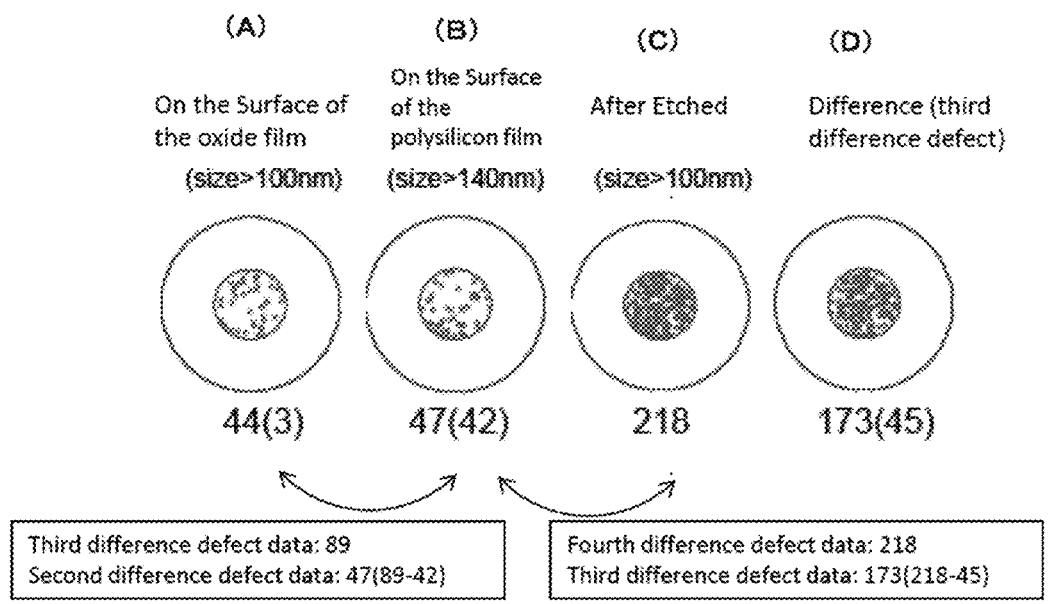
FIG. 5 is a diagram showing an example of a defect detection process.
Figure 6:
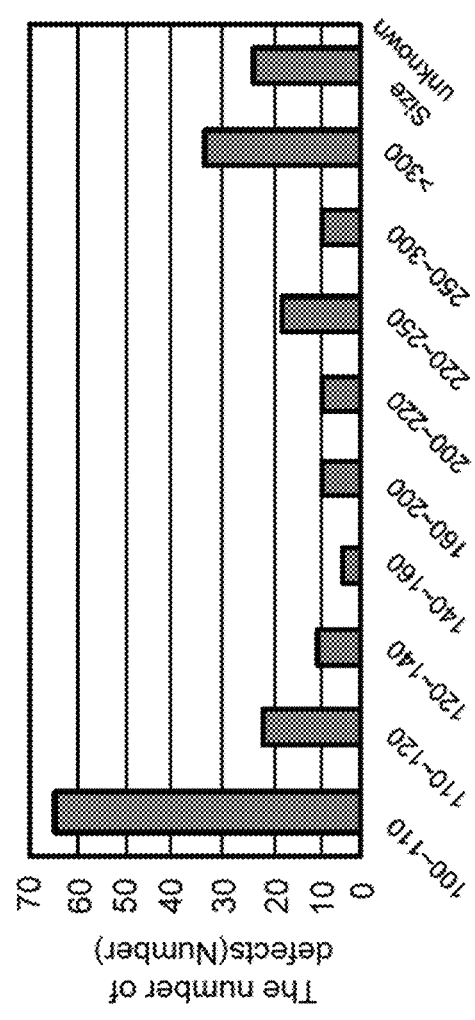
FIG. 6 is a graph showing the distribution of defect sizes in the defect detection results in FIG. 5.

Here, a specific example of the defect detection process is explained while referring to FIG. 5 and FIG. 6. FIG. 5 is a diagram which shows a detection result of the number of defects during etching of the silicon substrate 100 set in Slot 01, Slot 05 and Slot 09 which are boat addresses within the quartz boats 201 and 301. FIG. 6 is a graph which shows the distribution of differing defect sizes detected in the silicon substrate 100 set in Slot 01 in FIG. 5.

FIG. 5 (A) shows a detection process of defects after a bare silicon substrate 100 is set in Slot 01 of the quartz boat 201 in the thermal oxidation furnace 200 and an oxide film is formed. Raw data, that is, the number of the second defect data, of defects larger than 100 nm detected in the surface of the oxide film 101 is 47. The reference (3) shown in the diagram shows the number of defects larger than 100 nm detected in the surface of the bare silicon substrate 100, that is, the number of defects deleted where the coordinates match the first defect data. That is, while the total number of defects larger than 100 nm detected in the surface of the oxide film 101 of the silicon substrate 100 is 47, defects in three positions of which coordinates match the raw data (first defect data) of defects detected in the previous process are deleted. Here, the defect data obtained by reducing data of defects of which coordinates match the coordinates of the first defect data from the second defect data is defined as "first difference defect data".

Then, FIG. 5 (B) shows a detection process of defects after a silicon substrate is set in Slot 01 of the quartz boat 301 in the LPCVD device 300 and a polysilicon film is formed. Furthermore, the lower limit of defects which can be optically detected in the polysilicon film is 140 nm. Raw data, that is, the number of the third defect data, of defects larger than 140 nm detected in the surface of the polysilicon film 102 of the silicon substrate 100 is 89. The number (42) of defects shown in FIG. 5 (B) shows the number of defects of which coordinates among the third defect data match the first difference defect data of which defects is detected in the surface of the oxide film 101 of the silicon substrate 100 and is larger than 100 nm. Here, the defect data obtained by reducing data of defects of which coordinates match the coordinates of the first difference defect data from the third defect data is defined as "second difference defect data". The number of the second difference defect data in the case of FIG. 5 (B) is 47.

Then, FIG. 5 (C) shows a detection process of defects after the silicon substrate 100 in Slot 01 is etched. Raw data, that is, the number of the fourth defect data, of defects larger than 100 nm detected in the surface which is etched is 218. In the present embodiment, it is possible to consider data related to the 218 defects as defect data due to etching residue. Thus, a result of deleting the number (45) of defects of which coordinates match the coordinates of the second difference defect data detected from the surface of the polysilicon film 102 from the fourth defect data of the 218 defects detected on the etched surface is defined as third difference defect data. The number of the third difference defect data in the case of FIG. 5 (C) is 173. The third difference defect data is the number of defects remaining as a difference and the defects generated in the organic bottom anti-reflective coating 103 (FIG. 5 (D)). The defects remaining as a difference are referred to as difference defects herein.

Then, defects included in the difference defects 173 shown in FIG. 5 are classified into size categories (100~110 nm, 110~120 nm, 120~140 nm, 140~160 nm, 160~200 nm, 200~220 nm, 220~250 nm, 250~300 nm, >300 nm) and detected and the number of defects of each size are calculated and the result is shown in FIG. 6.

Therefore, by making it possible to detect the size and number of defects generated in an organic bottom anti-reflective coating using the defect examination method described above it is possible to evaluate the quality of the organic bottom anti-reflective coating. It is desirable to set the detection lower limit of a defect's size to a smaller value according to miniaturization of semiconductor devices.

Furthermore, in order to verify the relationship between a silicon substrate attached with a polysilicon film and a Haze value, film thickness and film formation temperature which are the conditions for forming a polysilicon film are respectively changed and a Haze value is measured and the relationship between film thickness of the polysilicon film and film formation temperature and a Haze value are evaluated.

Figure 7B:
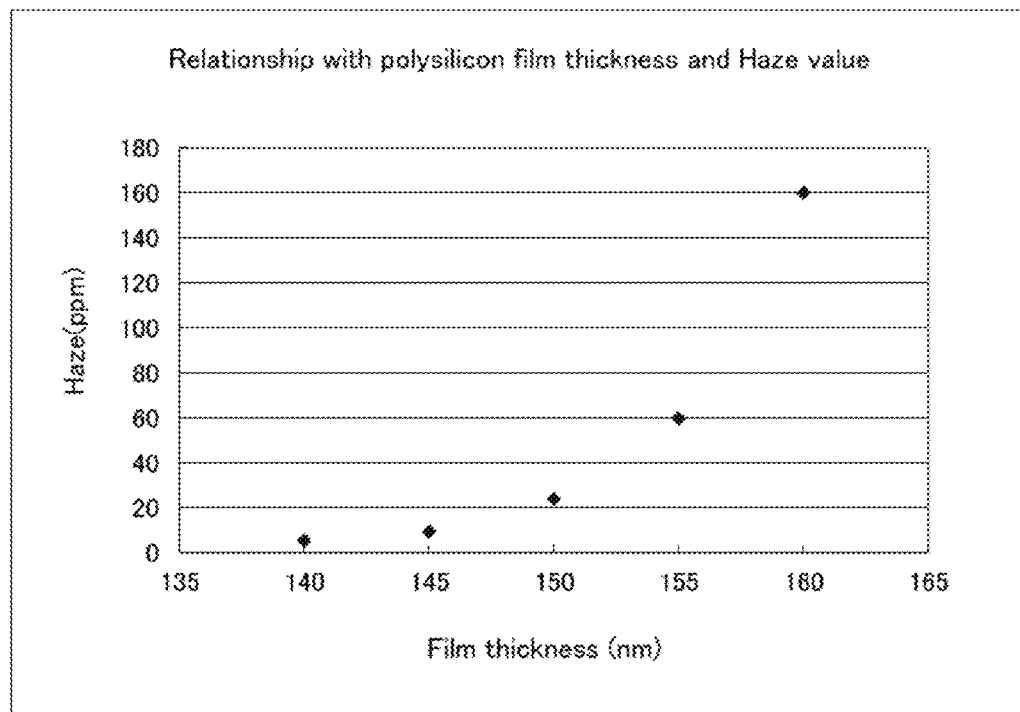
FIG. 7B is a diagram showing the relationship between the film thickness of a polysilicon film of the evaluation substrate and a Haze value related to one embodiment of the present invention.

The relationship film thickness of a polysilicon film and a Haze value is explained while referring to FIGS. 7A-7C. In FIG. 7A is a table which shows the measurement results of film thickness of a polysilicon film and a Haze value, in FIG. 7B is a diagram which graphs the table in FIGS. 7A and 7C is a table which shows the relationship between a Haze value and the detection lower limit of a defect. Furthermore, the film formation temperature of the polysilicon film shown in FIG. 7A is 615° C. According to the measurement results, a lowest Haze value of 5.5 ppm was confirmed when the film thickness of the polysilicon film was 140 nm. In addition, as is shown in FIG. 7C, it was confirmed that the detection lower limit of a defect decreases as the Haze vale decreases. In this case, it was confirmed that the detection lower limit was 1.2 μm in the case where the Haze value was 6 ppm. That is, it is clear that it is possible to reduce a Haze value by reducing the film thickness of a polysilicon film.

Then, the relationship between a film formation temperature of a polysilicon film and a Haze value is explained while referring to FIGS. 8A-8E and FIG. 9. FIGS. 8A~8E are the results of forming a polysilicon film on a plurality of silicon substrates attached with an oxide film set in the quartz boat 301 in the LPCVD device 300 shown in FIG. 4 and measuring film thickness and a Haze value. In this case, silicon substrates attached with an oxide film in four lots were set into the quartz boat 301 for each lot, the polysilicon film was formed and the film thickness and Haze value was measured for each lot.

FIG. 8A shows the results of measuring the film thickness and Haze value of a polysilicon film with respect to thirteen boat numbers 13, 17, 21, 25, 29, 33, 37, 41, 45, 49, 53, 57, 61 among the plurality of silicon substrates attached with an oxide film set in the quartz boat 301 as lot A. In lot A, with regards to the heating temperature of the heater 304 within the LPCVD device 300, each measured temperature of the four temperature sensors 305 was 616.5° C. at the top (U), 615.0° C. at the second stage (CU), 612.0° C. at the third stage (CL) and 603.2° C. at the bottom (L) with respect to a setting temperature of 615° C. In addition, the setting film thickness of the polysilicon film was 150 nm.

FIG. 8B shows the results of measuring the film thickness and Haze value of a polysilicon film with respect to five boat numbers 13, 17, 21, 25, 29 among the plurality of silicon substrates attached with an oxide film set in the quartz boat 301 as lot B. In lot B, with regards to the heating temperature of the heater 304 within the LPCVD device 300, each measured temperature of the four temperature sensors 305 was 621.5° C. at the top (U), 620.0° C. at the second stage (CU), 617.0° C. at the third stage (CL) and 604.2° C. at the bottom (L) with respect to a setting temperature of 620° C. In addition, the setting film thickness of the polysilicon film was 150 nm.

FIG. 8C shows the results of measuring the film thickness and Haze value of a polysilicon film with respect to thirteen boat numbers 13, 17, 21, 25, 29, 33, 37, 41, 45, 49, 53, 57, 61 among the plurality of silicon substrates attached with an oxide film set in the quartz boat 301 as lot C. In lot C, with regards to the heating temperature of the heater 304 within the LPCVD device 300, each measured temperature of the four temperature sensors 305 was 621.5° C. at the top (U), 620.0° C. at the second stage (CU), 617.0° C. at the third stage (CL) and 604.2° C. at the bottom (L) with respect to a setting temperature of 620° C. In addition, the setting film thickness of the polysilicon film was 150 nm.

FIG. 8D shows the results of measuring the film thickness and Haze value of a polysilicon film with respect to thirteen boat numbers 13, 17, 21, 25, 29, 33, 37, 41, 45, 49, 53, 57, 61 among the plurality of silicon substrates attached with an oxide film set in the quartz boat 301 as lot D. In lot D, with regards to the heating temperature of the heater 304 within the LPCVD device 300, each measured temperature of the four temperature sensors 305 was 621.5° C. at the top (U), 620.0° C. at the second stage (CU), 617.0° C. at the third stage (CL) and 608.0° C. at the bottom (L) with respect to a setting temperature of 620° C. In addition, the setting film thickness of the polysilicon film was 150 nm.

FIG. 8E shows the results of measuring the film thickness and Haze value of a polysilicon film with respect to four boat numbers 49, 53, 57, 61 among the plurality of silicon substrates attached with an oxide film set in the quartz boat 301 as lot E. In the lot D, with regards to the heating temperature of the heater 304 within the LPCVD device 300, each measured temperature of the four temperature sensors 305 was 621.5° C. at the top (U), 620.0° C. at the second stage (CU), 617.0° C. at the third stage (CL) and a low of 604.2° C. at the bottom (L) with respect to a setting temperature of 620° C. In addition, the setting film thickness of the polysilicon film was 140 nm.

Figure 10:
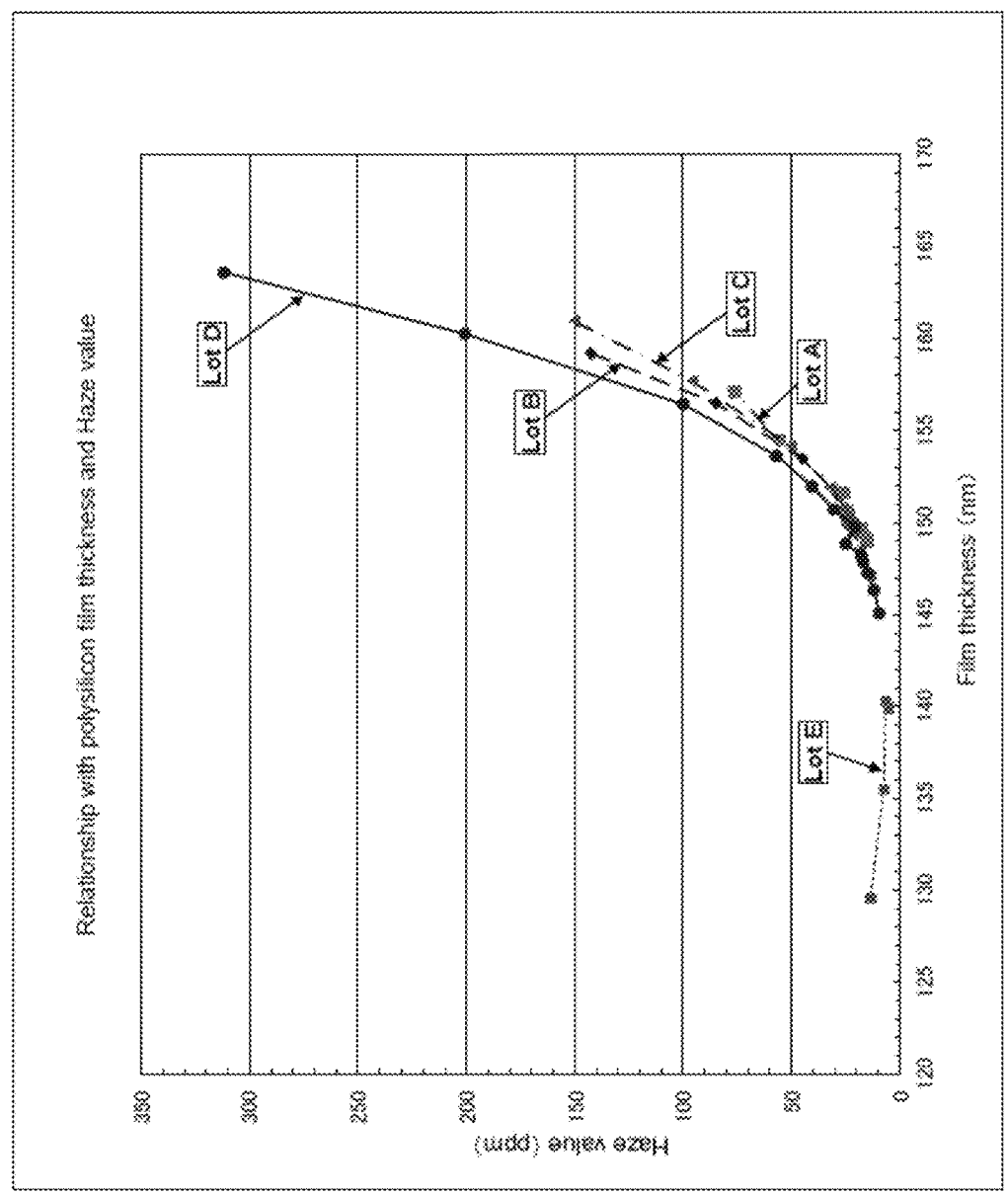
FIG. 10 is a graph plotting the measurement results of FIGS. 8A~8E.

FIG. 9 is a diagram where each measurement result in FIGS. 8A~8D are graphed. In the graph it is shown that a substrate with a Haze value of 30 ppm or less can be used (OK) as an evaluation substrate. From the film thickness and Haze value measurement results described above, it could be confirmed that when the distribution of Haze values between lot A in which a film formation temperature was set at 615° C. and lots B, C and D in which a film formation temperature was set at 620° C. is compared, the number of films which show a Haze value of 30 ppm or less was the largest in lot A and that the Haze value tended to decrease when the film formation temperature is decreased to 615° C. In addition, FIG. 10 is a diagram where each measurement result in FIGS. 8A~8E are graphed. Considering the distribution of Haze values in lot E in the graph, there is a possibility that a lowest or minimum Haze value exists.

According to the results in FIG. 8E and FIG. 10, there is a tendency for the Haze value to increase when the film thickness of a polysilicon film is set less than 140 nm. Thus, in order to investigate clearly the relationship between forming a thin filmed polysilicon film and a Haze value, a polysilicon film with a film thickness of about 129.0 nm to about 140.0 nm was formed and film thickness and Haze values of the polysilicon film were measured.

Figure 11B:
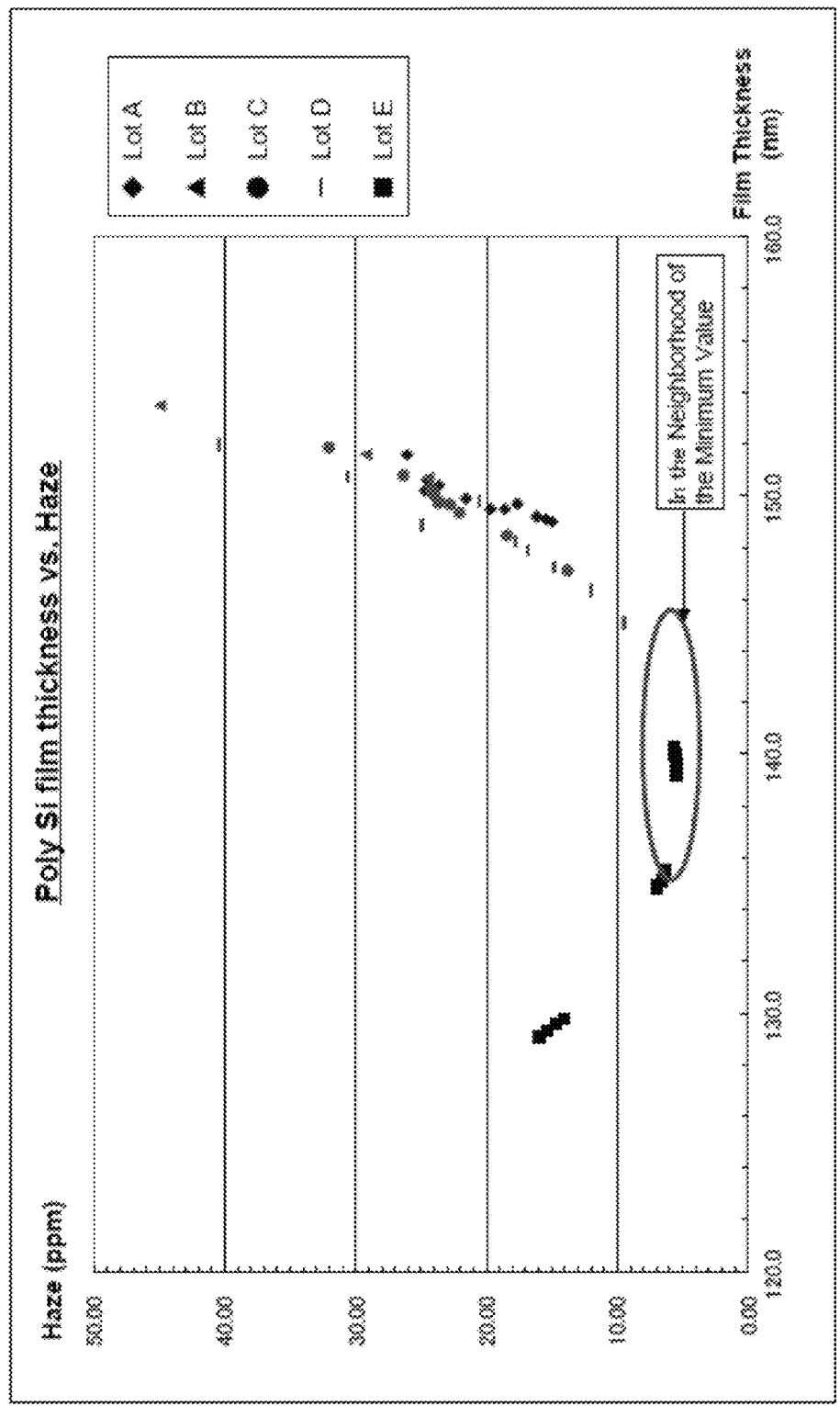
FIG. 11B is a graph showing the measurement results of a film thickness of and Haze value for a polysilicon film with a film thickness of about 129.0 nm to about 140.0 nm.

First, as lot F, the film formation temperature with respect to a plurality of silicon substrates attached with an oxide film set in the quartz boat 301 in the LPCVD device 300 shown in FIG. 4 was set to 615° C., a polysilicon film was formed and the film thickness and Haze value were measured. The measurement results of lot F and a part of the measurement results in FIGS. 8A to 8D are shown in FIG. 11B as a comparison. FIG. 11A shows the results of measuring the film thickness and Haze value of the polysilicon film in lot F. FIG. 11B is a table which shows the part which can be used for comparison from the measurement results in FIGS. 8A to 8D, that is, data where the Haze value is less than 50 ppm is extracted.

As is shown in FIG. 11B, the Haze value decreases when the film thickness is decreased and the Haze value is asymptotic to a minimum value as the film thickness becomes thinner. However, after the Haze value reaches a minimum, it was confirmed that the Haze value increases again by forming a thin polysilicon film.

Then, the relationship between a setting temperature when forming a polysilicon film and film thickness of a polysilicon film was examined as follows.

Figure 13:
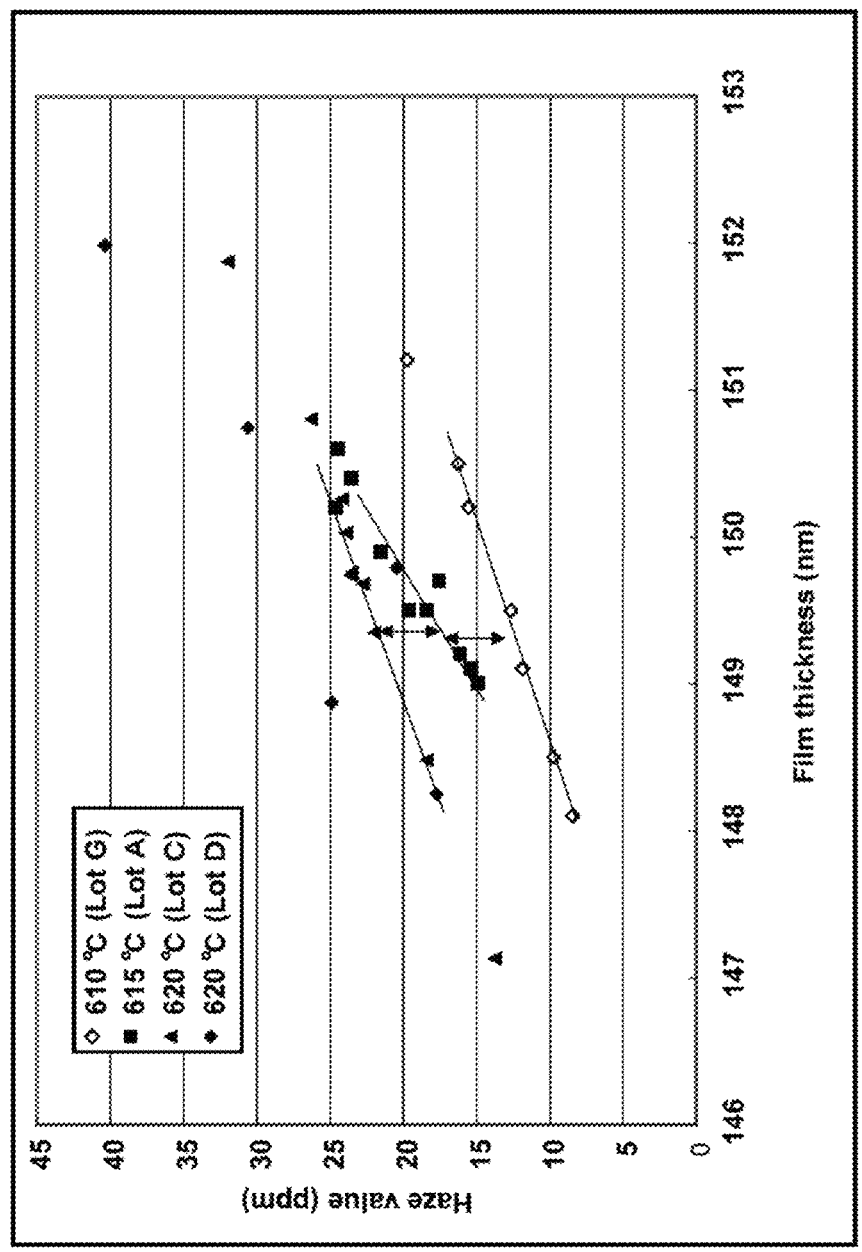
FIG. 13 is one part of a graph plotting the measurement results of FIG. 12 in addition to FIG. 9.

First, as lot G, the film formation temperature with respect to a plurality of silicon substrates attached with an oxide film set in the quartz boat 301 was set to 610° C., a polysilicon film was formed and the film thickness and Haze value of the polysilicon film were measured. The measurement results of lot G and a part of the measurement results in FIGS. 8A, C and D are shown in FIG. 12 and FIG. 13 as a comparison. FIG. 12 shows the results of measuring the film thickness and Haze value of the polysilicon film, which was formed at a film formation temperature 610° C. on a plurality of silicon substrates attached with an oxide film set in the quartz boat 301 of the LPCVD device 300 shown in FIG. 4. FIG. 12 is a table which shows the part which can be used for comparison from the measurement results in FIGS. 8A, 8C and 8D.

FIG. 12 shows the results of measuring film thickness and Haze values of a polysilicon film with respect to seven silicon substrates among the plurality of silicon substrates set in the quarts boat 301 as lot G. In lot G the heating temperature of the heater 304 within the LPCVD 300 device is a setting temperature of 610° C. and the set film thickness of the polysilicon film is 150 nm.

FIG. 13 is a diagram which graphs the measurement results shown in FIG. 12. In this case, as is shown in FIG. 13, the distribution of Haze values in the case where the film formation temperature is reduced from 620° C. to 610° C. in 5° C. decrement could be confirmed to drop the most to between 8.5 ppm~19.8 ppm.

As described above, when a polysilicon film is formed, it was confirmed that the Haze value decreases when the film formation temperature is decreased and when the film thickness setting is decreased. This relationship between the film formation temperature of a polysilicon film and a Haze value was further examined. The growth speed of a polysilicon film changes due to a film formation temperature and the surface roughness of the polysilicon film also changes. Because of this, the relationship between the surface roughness of a polysilicon film and a Haze value was examined further.

(Relationship between the surface state of a polysilicon film and a Haze value)

Figure 14:
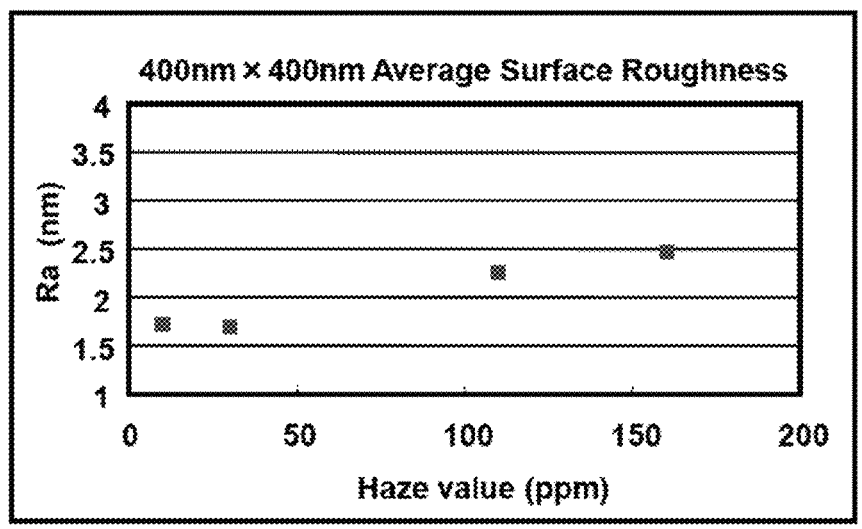
FIG. 14 is a table and graph showing the results of measuring surface roughness (R) of a polysilicon film and a Haze value.
Figure 15:
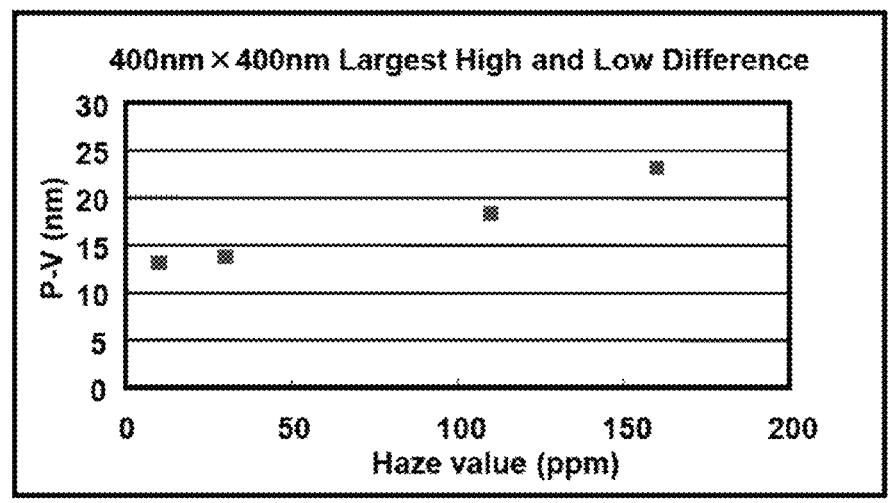
FIG. 15 is a table and a graph showing the results of measuring the largest high and low difference (P–V) of a polysilicon film surface and a Haze value.
Figure 16:
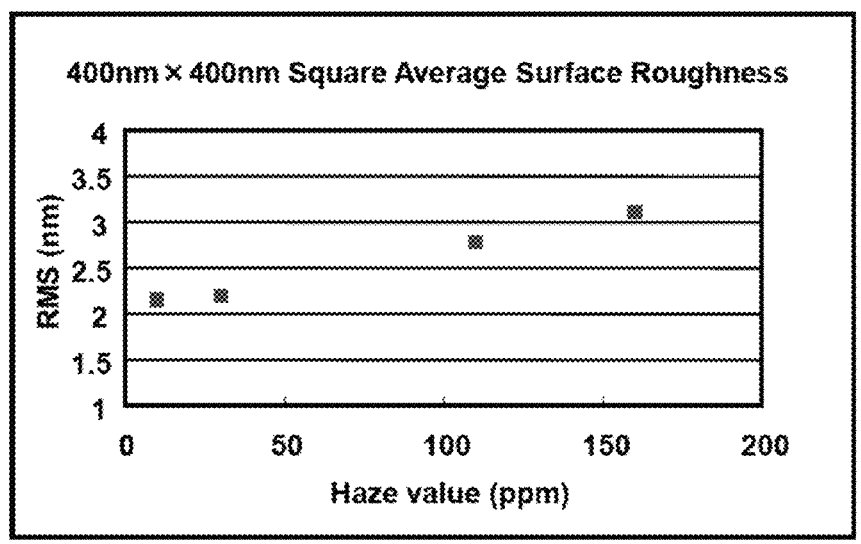
FIG. 16 is a table and graph showing the results of measuring a square surface roughness (RMS) of a polysilicon film and a Haze value.

FIG. 14~FIG. 16 are diagrams which show the results of measuring average surface roughness (Ra), a largest high and low difference (P–V value) and a square average surface roughness (RMS) as parameters which express the relationship between a surface state and Haze value of a silicon substrate attached with a polysilicon film formed at the same film formation temperature. The average surface roughness (Ra), largest high and low difference (P–V value) and a square average surface roughness (RMS) show the results of measuring four silicon substrates with a surface range of 400 nm×400 nm. The average surface roughness (Ra), largest high and low difference (P–V value) and a square average surface roughness (RMS) are values measured using an atomic force microscope (SPA460-DFM manufactured by Seiko Instruments Inc).

(1) Relationship Between Average Surface Roughness (Ra) and Haze Values

First, the results of measuring average surface roughness (Ra) and a Haze value of a silicon substrate attached with a polysilicon film are shown in FIGS. 14 (A) and (B). In FIG. 14, (A) is a table which shows the results of measuring average surface roughness (Ra) and a Haze value, and (B) is a diagram which graphs the results in (A). From the measurement results of average surface roughness (Ra) and Haze values of the polysilicon film shown in FIGS. 14 (A) and (B), it was clear that when average surface roughness (Ra) becomes smaller, the Haze value also tends to decrease. In this case, it was confirmed that in the case where average surface roughness (Ra) was 1.72 nm, the Haze value was a lowest value of 10 ppm.

(2) Relationship Between Largest High and Low Difference (P–V Value) and Haze Values Then, the results of measuring largest high and low difference (P–V value) and a Haze value of a silicon substrate attached with a polysilicon film are shown in FIGS. 15 (A) and (B). In FIG. 15, (A) is a table which shows the results of measuring largest high and low difference (P–V value) and a Haze value, and (B) is a diagram which graphs the results in (A). From the measurement results of largest high and low difference (P–V value) and Haze values of the polysilicon film shown in FIGS. 15 (A) and (B), it was clear that when largest high and low difference (P–V value) becomes smaller, the Haze value also decreases. In this case, it was confirmed that in the case where largest high and low difference (P–V value) was 13.2 nm, the Haze value was a lowest value of 10 ppm.

(3) Relationship Between Square Average Surface Roughness (RMS) and Haze Values

Then, the results of measuring square average surface roughness (RMS) and a Haze value of a silicon substrate attached with a polysilicon film are shown in FIGS. 16 (A) and (B). In FIG. 16, (A) is a table which shows the results of measuring square average surface roughness (RMS) and a Haze value, and (B) is a diagram which graphs the results in (A). From the measurement results of square average surface roughness (RMS) and Haze values of the polysilicon film shown in FIGS. 16 (A) and (B), it was clear that when square average surface roughness (RMS) becomes smaller, the Haze value also decreases. In this case, it was confirmed that in the case where square average surface roughness (RMS) was 2.15 nm, the Haze value was a lowest value of 10 ppm.

As described above, it was confirmed that a Haze value decreases when each value of the average surface roughness (Ra), largest high and low difference (P–V value) and a square average surface roughness (RMS) in a silicon substrate surface attached with a polysilicon film become smaller. That is, it was clear that as a condition for decreasing a Haze value it is effective to decrease the film formation temperature of a polysilicon film and planarize the surface of the polysilicon film. In addition, it can be considered from the results in FIG. 13 and FIG. 14 to FIG. 16 that even if the film thickness of the polysilicon film is the same, the higher the film formation temperature is set, the larger the grain diameter of the polyilicon becomes, and the average surface roughness (Ra), largest high and low difference (P–V value) and a square average surface roughness (RMS) become larger.

According to the evaluation substrate for evaluating defects in a bottom anti-reflective coating related to one embodiment of the present invention, in each formation process of an oxide film, polysilicon film and reflective film it is possible to store defects of a desired size and coordinates which show the position of the defects in each process, delete the defects which have matching coordinates in each film formation process and detect finally remaining defects as defects which are caused by foreign objects included in a bottom anti-reflective film. As a result, it is possible to evaluate only those defects which are caused by foreign objects included in a bottom anti-reflective film.

In addition, according to the evaluation substrate related to one embodiment of the present invention, the thickness and formation temperature of a polysilicon film was found to be related as a result of examining a decrease in a Haze value which affects a detection lower limit value of a defect size in a defect examination device. In addition, it was confirmed that when the film thickness and formation temperature of a polysilicon film is changed and a Haze value is measured, the Haze value decreases when film thickness and film formation temperature are decreased. Therefore, when manufacturing an evaluation substrate, it is possible to decrease the detection lower limit value of a defect size in a defect examination device by adjusting the film thickness and film formation temperature of a polysilicon film to the conditions where a Haze value decreases.

In addition, from the results of measuring the film thickness and film formation temperature of the polysilicon film described above and the average surface roughness (Ra), largest high and low difference (P–V value) and a square average surface roughness (RMS) in a polysilicon film, it was confirmed that a Haze value has a lowest value. That is, in the relationship between film thickness of the polysilicon film shown in FIGS. 7A-7C and a Haze value, it was confirmed that a Haze value decreases when film thickness is decreased and is asymptotic to a minimum value as the film thickness becomes thinner. However, from the relationship between film thickness of the polysilicon film shown in FIG. 10, FIGS. 11A and 11B and a Haze value, it was confirmed that a film thickness of the polysilicon film exists whereby the Haze value becomes a lowest value and that there is a limit to the effect of decreasing Haze value due to forming a thin polysilicon film.

In addition, in the relation between the film formation temperature of the polysilicon film shown in FIG. 9 and FIG. 13 and a Haze value, it was confirmed that the Haze value decreases when the film formation temperature is decreased and the Haze value becomes a lowest value when the film formation temperature is set to its lowest value. In the relationship between average surface roughness (Ra) of the polysilicon film shown in FIG. 14 and a Haze value, it was confirmed that a Haze value becomes a lowest value when average surface roughness (Ra) is 1.71 nm. In the relationship between a largest high low difference (P–V value) shown in FIG. 15 and a Haze value, it was confirmed that a Haze value becomes a lowest value when a largest high low difference (P–V value) is 13.2 nm or less. In the relationship between a square average surface roughness (RMS) shown in FIG. 15 and a Haze value, it was confirmed that a Haze value becomes a lowest value when a square average surface roughness (RMS) is 2.15 nm or less. Furthermore, apart from a polysilicon film, a Haze value becomes smaller in the case where the conditions of average surface roughness (Ra), largest high low difference (P–V value) and square average surface roughness (RMS) are satisfied even in the case of an amorphous silicon film which does not have grain boundaries and as a result it is possible to reduce the detection lower limit value of foreign materials.

Therefore, by setting the film formation conditions for decreasing film thickness, film formation temperature, average surface roughness (Ra), largest high low difference (P–V value) and square average surface roughness (RMS) of a polysilicon film, respectively, it is possible to reduce a Haze value which affects the detection lower limit value of a defect's size in a defect examination device to a lowest value and decrease the detection lower limit value of a defect's size in a defect examination device. As a result, by using the evaluation substrate related to one embodiment of the present invention it is possible to detect defects with an even smaller size in an organic bottom anti-reflective coating. By using the detection effects of defects with this evaluation substrate, it is possible to appropriately evaluate quality with respect to defects (including dust and depressions etc) included in the organic bottom anti-reflective coating which is formed. By reflecting the results of a quality evaluation of an organic bottom anti-reflective coating in the manufacturing process of a semiconductor device, it is possible prevent in advance deteriorations of semiconductor device quality caused by an organic bottom anti-reflective coating. In addition, by decreasing the detection lower limit value of a defect included in an organic bottom anti-reflective coating, it is possible to guarantee detection of foreign material defects included in an organic bottom anti-reflective coating which affects the manufacturing process in response to miniaturization of semiconductor devices and improve the reliability of the manufacturing process.

In addition, in the evaluation substrate of the embodiment described above, the thickness of a polysilicon film may be larger than the thickness of an oxide film in order to decrease the detection lower limit value of a foreign material defect. By combining the conditions related to the film thickness of a polysilicon film and oxide film with any one of the film formation conditions related to average surface roughness (Ra), largest high low difference (P–V value) and square average surface roughness (RMS), it is possible to decrease the detection lower limit value of a defect's size in a defect examination device and the detection lower limit value of a defect included in an organic bottom anti-reflective coating.

The structure of the evaluation described above is illustrative. When each of films formed on a substrate is called a first film and a second film in order from the side of the substrate, the first film is set so that the etching rate of the first film is lower than the etching rate of the second film with respect to the etchant used in etching the second film and the detection lower limit value of a defect which can be optically detected may be the same or less than the detection lower limit value of a defect of the second film. The reason for these settings is that it is possible to use the first film as an etching stopper and for detecting with good accuracy foreign materials included in an organic material formed on the second film without affecting the characteristics of the first film. There are no particular limitations to the substrate used in the evaluation substrate and the silicon substrate of the present invention is merely for illustrative purposes. More preferably, the substrate may be provided with a surface which reflects the laser light used in a defect examination device described below.

(Defect Examination Device)

Figure 17:
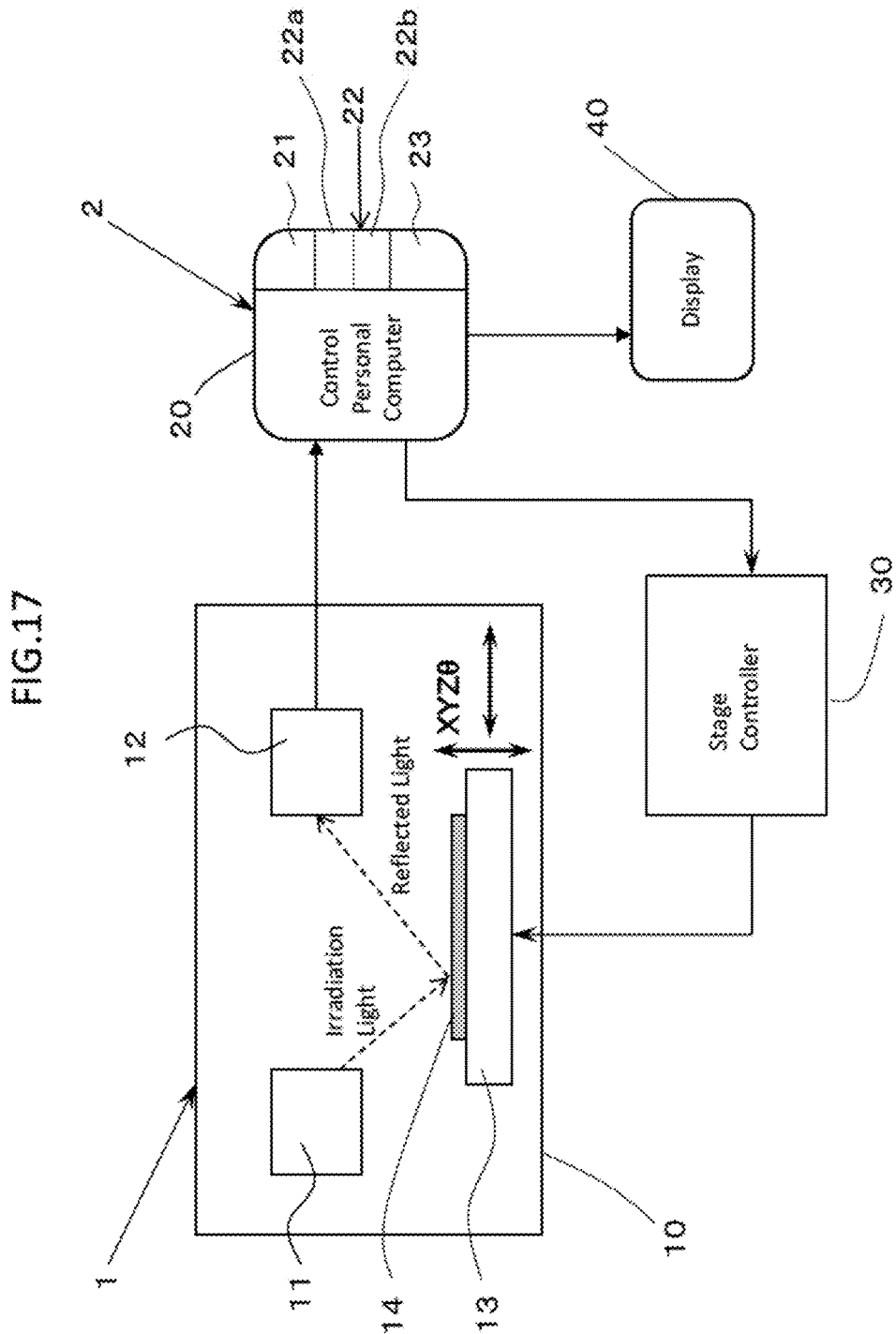
FIG. 17 is a diagram showing an example of the structure of a defect examination device related to one embodiment of the present invention.

The defect examination device can be favorably realized using the defect examination device having the structure shown in FIG. 17.

That is, a light source 11, a stage 13 on which an object to be measured 14 is placed and a light detection part 12 which detects light reflected from the object to be measured 14 are arranged within a housing 10 such as a vacuum pump, and a defect detection means 1 is structured to include these devices. The object to be measured 14 is not particularly limited and a single substrate such as a silicon substrate, a substrate formed with a silicon oxide film, a substrate formed with a plurality of films such as a substrate formed with a polysilicon film on this silicon oxide film or a substrate on which the plurality of films have been etched can be exemplified.

The light source 11 emits a probe light. Preferably, the light source 11 emits light with a high level of directionality such as the laser described above. The light detection part 12 includes a light receiving unit such as a photon multiplier tube which receives light reflected from the object to be measured 14.

Defect data for each position on a surface of the object to be measured 14 obtained from the defect detection part 1 is stored in the defect data process means 2 and a process is performed such as comparing this defect data with defect data for each position on a surface of a second object which becomes an object to be measured for comparison.

The defect data process means 2 includes a first storage part 21, a comparison operator 22 which performs a comparison calculation described below, and a second storage part 23 which stores the calculation results output from the comparison operator 22.

The first storage means 21 can stores defect data for each position on a surface with respect to each object to be measured 14. For example, the object to be measured 14 is changed to a single substrate such as a silicon substrate, a silicon oxide film formed on the silicon substrate, a polysilicon film on the silicon oxide film or a film which exists on a substrate after being subjected to such a treatment as forming an organic film from an organic material on the polysilicon film followed by etching the substrate with the formed organic film, and then defect data with respect to each object to measured 14 is obtained and stored in the first storage part 21 as another object to be measured. That is, each time the object to be measured 14 is changed, respective defect data with respect to "the first object", "the second object", "the third object", "the $N^{th}$ object" is stored in the first storage part 21.

The comparison operator 22 compares defect data for each position on a surface of a $(N-1)^{th}$ object (N is an integer and N≥2) as a first object with defect data for each position on a surface of a $N^{th}$ object as a second object which is subjected to the treatment that a film is formed on the $(N-1)^{th}$ object or the treatment that the film as the $(N-1)^{th}$ object is etched and the comparison operator 22 performs difference calculations.

Specifically, the comparison operator 22 can perform difference calculations by deleting defect data which is common with defect data of a surface of the $(N-1)^{th}$ object among the defect data of a surface of the $N^{th}$ object from the defect data of a surface of the $N^{th}$ object.

Alternatively, the comparison operator 22 performs difference calculations by comparing defect data for each position on a surface of the first object with defect data for each position on a surface of the second object after such as a process for forming a film on the first object is performed or a process for etching a film formed as the first object is performed. The comparison comparator 22 defines this difference operation result as "first difference defect data". In addition, the comparison operator 22 can perform a difference calculation by deleting the first difference defect data of which position is common with defect data of a surface of a third object and which includes defects of a predetermined size among the first difference defect data from defect data of the surface of the third object.

The comparison operator 22 defines the difference calculation result related to the defect data of the surface of the third object and the first difference defect data as "second difference defect data". In this way, the comparison operator 22 performs a difference calculation by deleting defect data having positional commonality with $(P-2)^{th}$ difference defect data and having a predetermined defect size from defect data of a surface of a $P^{th}$ object (P is an integer and P≥3) stored in the first storage part 21. The operation result is defined in sequence as $(P-1)^{th}$ difference defect data.

Data of the result of a difference calculation by the comparison operator 22 is stored in the second storage part 23. In this way it is possible to extract defects caused by processes performed on the $N^{th}$ object by comparing the $N^{th}$ object with the $(N-1)^{th}$ object.

In addition, it is possible form the comparison operator 22 by combining a plurality of functionally different operation parts. For example, a first comparison operator 22a compares defect data for each position of a first object surface with defect data for each position of a second object surface having undergone a predetermined process performed on the first object, a difference calculation is performed with respect to defects at the same position and defects caused by a process performed on the second object are extracted.

In addition, a second comparison operator 22b compares defect data calculated and extracted by the first comparison operator part with defect data for each position of a third object surface having undergone a predetermined process performed on the second object, a difference calculation is performed with respect to defects at the same position and defects caused by a process performed on the second object are extracted.

Difference defect data is stored in the second storage part 23. If necessary a read process may be performed from the second storage part 23 and used in an calculation process of the comparison operator 22 with respect to the next object.

The defect data process means 2 can be realized by a control personal computer 20 etc and it is possible to display the obtained defect data or calculation results of the comparison operator 40 on a display connected to the personal computer.

In addition, it is possible to adjust the incline angle of the stage 13 or shift the position of the stage 13 in a horizontal or perpendicular direction using a stage controller 30 ("XYZθ" in FIG. 17). In this way, it is possible to sufficiently or appropriately obtain defect data for each position of a surface of the object to be measured 14 by changing the relative positional relationship between at least the light source 11 or the light detection part 12 and the object to be measured 14 using the stage controller 30. The stage controller 30 can be controlled using a control personal computer 20.

The evaluation substrate, foreign material examination method and defect examination device related to the present invention were explained above. Although the case of using an evaluation substrate comprised of a polysilicon film (first layer)/silicon oxide film (second layer))/silicon substrate was explained as the foreign material examination method of the present invention, the structure of the evaluation substrate may be different depending on the semiconductor device. The foreign material examination method of the present invention can detect foreign materials included in an organic material using evaluation substrates of various structures. For example, polysilicon, tungsten (W), aluminum (Al), molybdenum (Mo) may be used as a first layer and a silicon oxide film, nitride film, oxide film plus nitride film or a stacked layers of these may be used as a second layer.

In addition as explained above, the case where each of the first film and the second film of the evaluation substrate related to one embodiment of the present invention is formed of a single layer composed of a single material was explained. However, in another embodiment, it is possible to use a stacked structure of a plurality of layers formed from several materials other than a single layer structure formed from a single material as the first and second films. In addition, it is possible to use an inorganic material substrate such as a metal substrate, glass substrate, quartz substrate, alumina substrate, titania substrate or silicon substrate, an organic material substrate such as a plastic substrate or a composite substrate formed from an inorganic and organic material as the substrate of the present invention.

In addition, it is possible to use the materials exemplified in FIG. 18 as the second film, that is, a thermal oxide film (Th-$SiO_2$), $Si_3N_4$, $SiO_2$ film obtained from silicic add tetraethyl (TEOS-$SiO_2$), tantalum (Ta), a Cu thin film formed by a PVD method, a stacked layer thin film of TiN and Ti (TiN/Ti), SOI (single-crystal silicon formed on an insulation film) or amorphous silicon.

In addition, as described above, the film which includes an organic material formed on the second film of the evaluation substrate related to one embodiment of the present invention was explained using the case of an organic bottom anti-reflective coating formed on a polysilicon film. However, in another embodiment it is possible to use an organic material comprised from a single component, an organic material comprised from several components, or a composite material comprised from an inorganic material comprised of a ceramic and or a metal and an organic material as the film including an organic material of the present invention.

The results of measuring defects in each film stacked on a wafer substrate using a defect examination device were used in the embodiments described above. However, even if the measurement wavelength of the laser light source or light reception system used in the defect examination device are different, the detection sensitivity of the defect examination device is cyclically changed by the film thickness of the object to be measured. The same can be said with respect to a polysilicon film which has an easily changeable Haze value since here is a correlation between film thickness and the detection sensitivity of the defect examination device. In addition, the lower limit of the detection sensitivity of an optical defect examination device changes as is shown in FIG. 18 according to the type of single layer film formed on a silicon substrate. Therefore, it is sufficient to optimize the film thickness to be evaluated in accordance with the measurement results of the defect examination device in each film. As a result, while the film thickness of an oxide film was set to 80 nm and the film thickness of a polysilicon film was set to 150 nm in the above experiment, these film thicknesses may be arbitrarily changed in accordance with the evaluation results of the defect examination device.

(Manufacturing Method of a Semiconductor Device)

A manufacturing method of a semiconductor device includes various manufacturing processes depending on the device. In these manufacturing processes, for example, the present invention can be applied as follows. Data related to foreign materials included in an organic material is obtained using the defect examination method related to the present invention. In addition, the formation conditions of an organic material film, the material and formation conditions of a photo resist and formation conditions of a gate layer are set from the detection results of defects obtained using the defect examination method related to the present invention. Based on the set conditions, a gate insulation film is formed after cleaning a wafer substrate. A gate electrode layer is formed on the gate insulation film, and an organic material film and photo resist are formed on the gate electrode layer as a bottom anti-reflective coating. After etching the photo resist, the gate layer is patterned and a gate electrode is formed and the semiconductor device is manufactured.

It is possible to exemplify a semiconductor memory which uses the functions of a field effect transistor as an example of the semiconductor device manufactured using this manufacturing method. A field effect transistor can be manufactured by preparing a p type silicon substrate, doping impurities into the silicon substrate, forming a n type source and drain region, forming a gate insulation film by forming an insulation film comprised of silicon oxide on the silicon substrate and patterning the insulation film, and forming a conductive film comprised from a conductive material such as polysilicon formed through a known film formation method on the gate insulation film. It is possible to use the defect examination method of the present invention in the formation processes of the source region, drain region and gate insulation film described above.

What is claimed is:

1. An evaluation substrate for detecting a defect caused by a foreign object included in an organic material comprising:
    a silicon substrate
    a silicon oxide film arranged on the silicon substrate; and
    a polysilicon film arranged on the silicon oxide film,
    wherein a film containing an organic material is formed on the polysilicon film;
    a Haze value of a surface of the polysilicon film being 30 ppm or less.

2. The evaluation substrate according to claim 1, wherein an average surface roughness (Ra) of the polysilicon film is 1.73 nm or less.

3. The evaluation substrate according to claim 1, wherein the largest high and low difference (P-V value) of the polysilicon film is 13.8 nm or less.

4. The evaluation substrate according to claim 1, wherein a square surface roughness (RMS) of the polysilicon film is 2.2 nm or less.

5. The evaluation substrate according to claim 1, wherein a thickness of the polysilicon film is larger than a thickness of the silicon oxide film.

* * * * *